US011826568B2

(12) United States Patent
Velasco Valcke

(10) Patent No.: US 11,826,568 B2
(45) Date of Patent: Nov. 28, 2023

(54) TISSUE-STIMULATING METHOD USING FREQUENCY SCANNING OF ELECTRIC AND MAGNETIC FIELDS

(71) Applicant: PANACEA QUANTUM LEAP TECHNOLOGY LLC, Dallas, TX (US)

(72) Inventor: Francisco Javier Velasco Valcke, Bogotá (CO)

(73) Assignee: Panacea Quantum Leap Technology LLC, Dallas, TX (US)

( * ) Notice: Subject to any disclaimer, the term of this patent is extended or adjusted under 35 U.S.C. 154(b) by 32 days.

(21) Appl. No.: 16/967,761

(22) PCT Filed: Feb. 7, 2019

(86) PCT No.: PCT/IB2019/051007
§ 371 (c)(1),
(2) Date: Aug. 6, 2020

(87) PCT Pub. No.: WO2019/155407
PCT Pub. Date: Aug. 15, 2019

(65) Prior Publication Data
US 2021/0038892 A1    Feb. 11, 2021

(30) Foreign Application Priority Data
Feb. 7, 2018    (CO) .................. NC2018/0001283

(51) Int. Cl.
*A61N 1/36* (2006.01)
*A61N 2/00* (2006.01)
(Continued)

(52) U.S. Cl.
CPC .......... *A61N 1/36034* (2017.08); *A61N 1/06* (2013.01); *A61N 2/002* (2013.01); *A61N 5/00* (2013.01)

(58) Field of Classification Search
CPC ...... A61N 1/36034; A61N 1/06; A61N 2/002; A61N 5/00
See application file for complete search history.

(56) References Cited

U.S. PATENT DOCUMENTS

| 6,520,911 B1 * | 2/2003 | Wen ..................... G01V 3/082 600/437 |
| 7,333,852 B2 | 2/2008 | Palti |

(Continued)

FOREIGN PATENT DOCUMENTS

| JP | H0639042 A2 | 2/1994 |
| JP | 2000-510747 A2 | 8/2000 |

(Continued)

OTHER PUBLICATIONS

Ingber, Donald E., "Can cancer be reversed by engineering the tumor microenvironment?," Semin Cancer Biol. Oct. 2008; 18(5): 356-364.

(Continued)

*Primary Examiner* — Allen Porter
*Assistant Examiner* — Adreanne A. Arnold
(74) *Attorney, Agent, or Firm* — Maine Cernota & Curran

(57) ABSTRACT

Methods and devices for tissue stimulation with electromagnetic fields by frequency scan are described. The frequency scan refers to the variation of the electromagnetic field applied to a tissue via increments in frequency deltas, which adapts to tissue impedance response feedback. In addition, some methods allow determining stimulation frequency bands in order to focus stimuli in bands until the tissue impedance response returns to a tolerance level or exceeds a maximum stimulation time.

51 Claims, 18 Drawing Sheets

(51) Int. Cl.
 *A61N 1/06* (2006.01)
 *A61N 5/00* (2006.01)

(56) References Cited

U.S. PATENT DOCUMENTS

| | | | |
|---|---|---|---|
| 2001/0023362 A1* | 9/2001 | Kobayashi | A61N 1/36034 |
| | | | 607/72 |
| 2005/0278001 A1 | 12/2005 | Qin et al. | |
| 2006/0085049 A1* | 4/2006 | Cory | A61B 5/4041 |
| | | | 607/48 |
| 2010/0152817 A1 | 6/2010 | Gillbe | |
| 2014/0330345 A1* | 11/2014 | John | A61N 1/36082 |
| | | | 607/59 |
| 2016/0106976 A1 | 4/2016 | Kucklick | |
| 2018/0000347 A1* | 1/2018 | Perez | A61N 1/36014 |

FOREIGN PATENT DOCUMENTS

| | | | | |
|---|---|---|---|---|
| JP | 2008-543386 A2 | 12/2008 | | |
| WO | 2005102452 A1 | 11/2005 | | |
| WO | WO-2014145284 A2 * | 9/2014 | | A61N 2/002 |
| WO | WO-2017/142948 A1 | 8/2017 | | |
| WO | WO-2017142948 A1 * | 8/2017 | | A61N 1/0556 |

OTHER PUBLICATIONS

Kadir, Lina Abdul, et al., "*Emerging Roles of the Membrane Potential: Action Beyond the Action Potential*," Front. Physiol., Nov. 21, 2018, vol. 9.
Kirson, Eilon D., et al., "*Alternating electric fields arrest cell proliferation in animal tumor models and human brain tumors*," PNAS Jun. 12, 2007 104 (24) 10152-10157.
Lobikin, Maria, et al., "*Resting Potential, Oncogene-induced Tumorigenesis, and Metastasis: The Bioelectric Basis of Cancer in vivo*," Phys Biol. Dec. 2012; 9(6): 065002.
Novocure "TTFields: a radical new approach to cancer treatment using electric fields," 2017, retrieved from URL <https://biopharmadealmakers.nature.com/users/38001-novocure/posts/16531-ttfields-a-radical-new-approach-to-cancer-treatment-using-electric-fields>.
Yang, M., et al., "Membrane potential and cancer progression," frontiers in Physiology, vol. 4, Article 185, 2013, pp. 1-10.
International Search Report / Written Opinion dated Aug. 26, 2019 for PCT/IB2019/051007.
Japan Patent Office, Office Action for Japanese Patent Application No. 2020-542637, dated Nov. 24, 2022.
Japan Patent Office, Written Opinion for Japanese Patent Application No. 2020-542637, dated May 29, 2023.

* cited by examiner

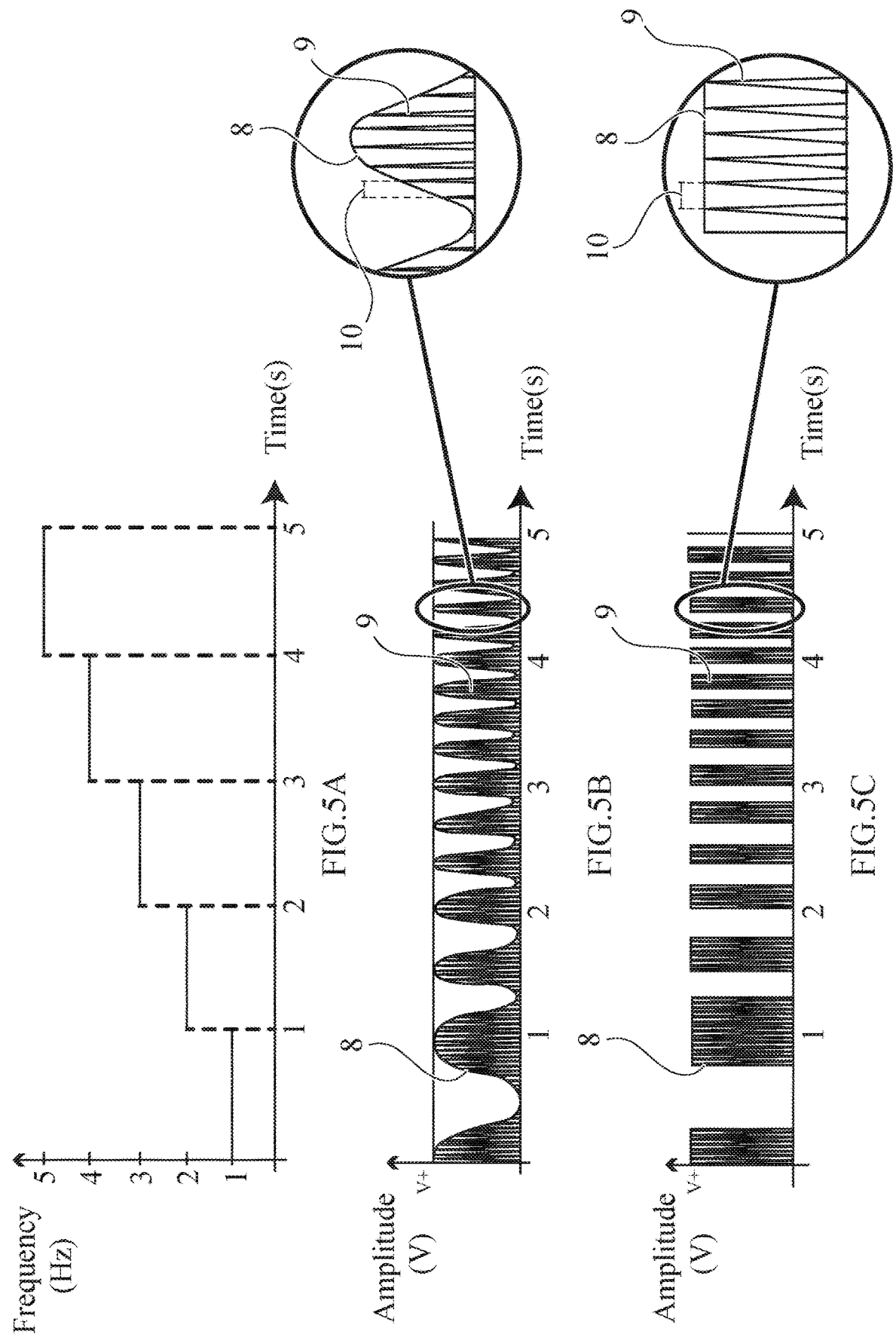

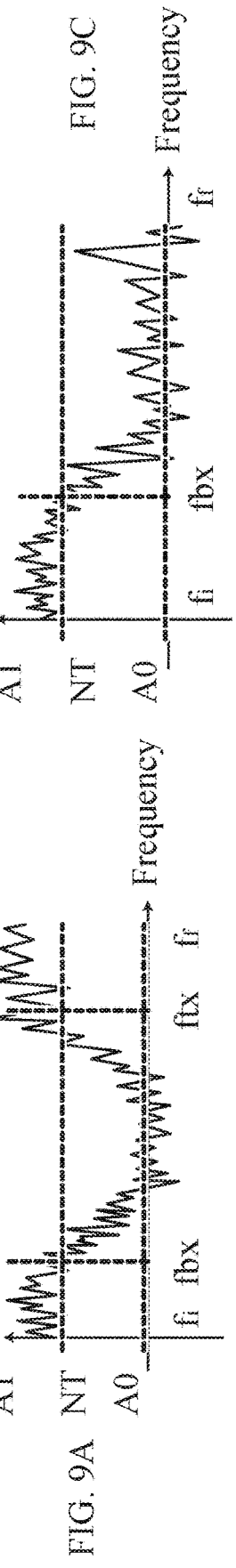
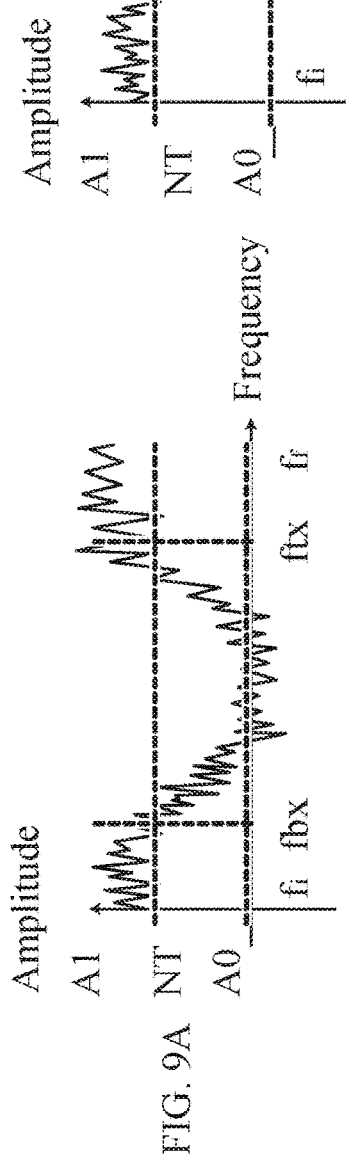
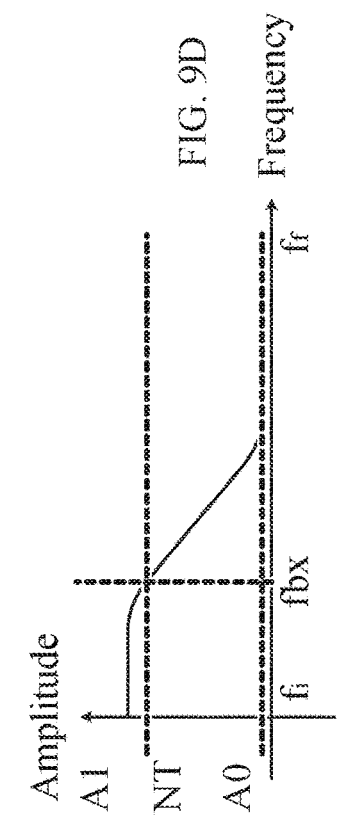
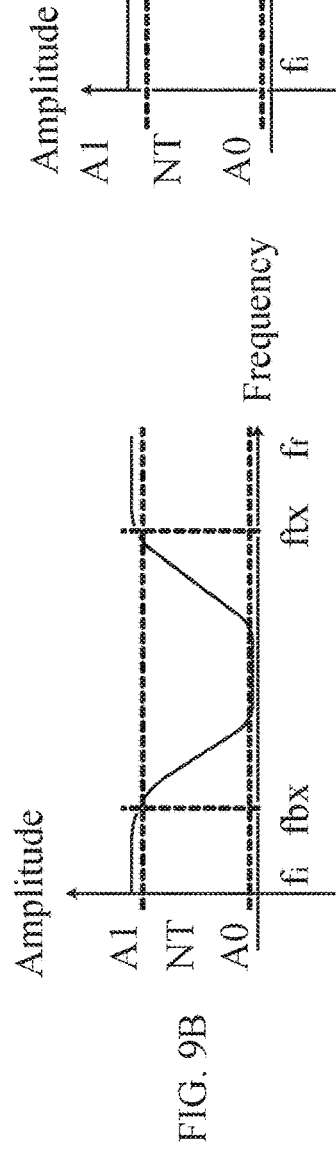
FIG. 9A
FIG. 9B
FIG. 9C
FIG. 9D

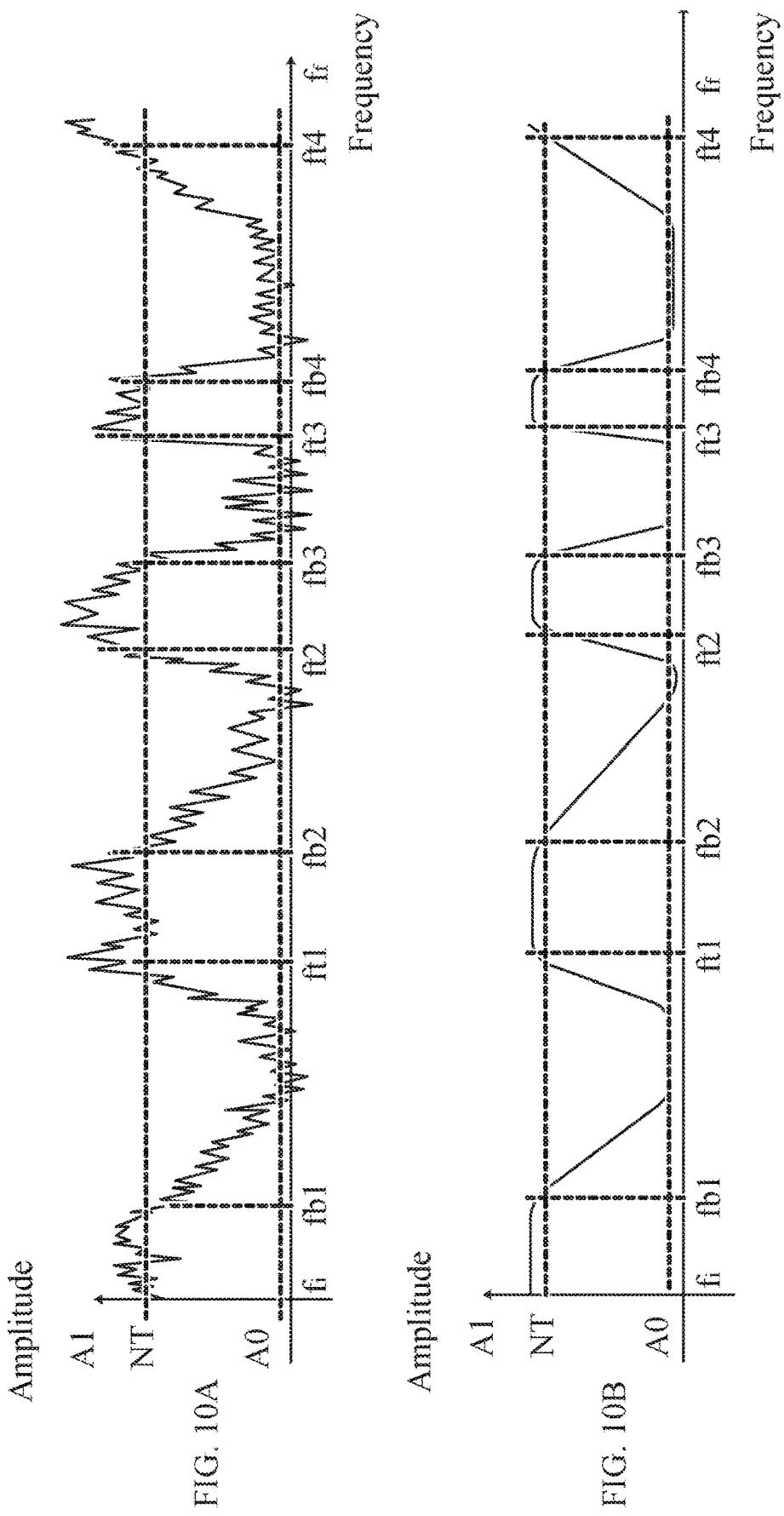

TISSUE-STIMULATING METHOD USING FREQUENCY SCANNING OF ELECTRIC AND MAGNETIC FIELDS

CROSS-REFERENCE TO RELATED APPLICATION

This application is the National Stage of International Application No. PCT/IB2019/051007, filed Feb. 7, 2018, and claims the priority benefit of Colombia application serial no. NC2018/0001283, filed on 7 Feb. 2018. The entirety of each of the above-mentioned patent applications is hereby incorporated by reference herein and made a part of this application. The tissue stimulation disclosed in the present document is related to the Colombian application serial no. NC2018/0001282, filed on 7 Feb. 2018.

The tissue stimulation disclosed in the present document is related to the Colombian application serial no. NC2018/0001282, filed on 7 Feb. 2018.

BACKGROUND

Technical Field

This disclosure is related to methods for tissue stimulation with electromagnetic, electric and magnetic fields by frequency scan, said frequency scan referring to the variation of the electromagnetic field, electric field or magnetic vector, via increments in frequency deltas from an initial stimulation frequency to a final stimulation frequency. These methods of stimulation have applications for identifying tissue anomalies and potentially correcting such anomalies, including, for example, identification of cancerous tissue and reversing growth and proliferation of said tissue.

Description of Related Art

It is well reported that changes to the electrical environment of the cell can affect the normal standing homeostasis of the cell. More specifically, cell homeostasis is related to the maintenance of a healthy resting membrane potential, and changes to this membrane potential have connections to uncontrolled cellular proliferation and differentiation (metastasis). As reported by Yang and Brackenbury (2013):

"Membrane potential (Vm), the voltage across the plasma membrane, arises because of the presence of different ion channels/transporters with specific ion selectivity and permeability. Vm is a key biophysical signal in non-excitable cells, modulating important cellular activities, such as proliferation and differentiation. Therefore, the multiplicities of various ion channels/transporters expressed on different cells are finely tuned in order to regulate the Vm. It is well-established that cancer cells possess distinct bioelectrical properties. Notably, electrophysiological analyses in many cancer cell types have revealed a depolarized Vm that favors cell proliferation. Ion channels/transporters control cell volume and migration, and emerging data also suggest that the level of Vm has functional roles in cancer cell migration. . . . Given that the fluctuation of Vm can functionally regulate tumorigenesis, differentiation, and promote cancer progression, it may serve as a potential marker for tumor detection and treatment, with prognostic value."

Beyond simply detecting tissue anomalies, the literature has also generally suggested that affecting the cellular environment to produce hyperpolarization of the cell membrane can actually reverse the development of tumors and metastasis (see e.g., Ingber, *Can cancer be reversed by engineering the tumor microenvironment?*, Semin Cancer Biol. 2008 October; 18(5): 356-364; Lobikin, Chernet, Lobo and Levin, *Resting Potential, Oncogene-induced Tumorigenesis, and Metastasis: The Bioelectric Basis of Cancer in vivo*, Phys Biol. 2012 December; 9(6): 065002; and, Kadir, Stacey and Barrett-Jolley, *Emerging Roles of the Membrane Potential: Action Beyond the Action Potential*, Front. Physiol., 21 Nov. 2018). Lobikin et al. (2012) specifically state, ". . . a mechanistic dissection of pathways by which the host reboots cancer cells may give rise to strategies that normalize cancer [citations deleted], in contrast to current approaches that seek to kill tumors and thus risk a compensatory proliferation response by any remaining cancer cells. . . . Most excitingly, forced hyperpolarization . . . via either molecular-genetic or pharmacological means can functionally reduce tumor incidence. . . . It is hoped that by unraveling fundamental roles of bioelectricity in pattern formation, biomedicine will someday be able to activate at will the remarkable pathways that highly regenerative model species use to normalize, not kill, tumor tissue . . . ."

The prior art, such as the articles cited above, is replete with suggestions to use pharmaceutical and molecular biology tools targeting ion-channels to regulate membrane potential and obtain the anti-cancer results suggested above. However, the proposed solutions applying electrical fields to identify cancerous tissue or attempt to reverse tumor formation is much more limited. Kadir et al. (2018) mentions, "even as far back as the late 1930s tumors were detected based on their voltmeter readings (Burr et al., 1938; Burr, 1940)." More recently, the application of electrical fields for treating cancer has been proposed and implemented, for example, by Palti in U.S. Pat. No. 7,333,852B2 (designated as tumor treating fields or TTFs). Clinical results of these TFs are described in the publication, Kirson, Dbalý, Tovaryš, Vymazal, Soustiel, Itzhaki, Mordechovich, Steinberg-Shapira, Gurvich, Schneiderman, Wasserman, Salzberg, Ryffel, Goldsher, Dekel and Palti, Alternating electric fields arrest cell proliferation in animal tumor models and human brain tumors, PNAS Jun. 12, 2007 104 (24) 10152-10157. The tumor inhibitory effect of TTFields has been principally attributed to two separate mechanisms: interference with the formation of the mitotic spindle microtubules and physical destruction of cells during cleavage, both of which are strongly dependent on the orientation of mitosis axis versus the field vectors. According to information provided by Novocure, a company commercializing a TTF solution under the OPTUNE trademark and assignee of the '852 patent mentioned above, in "TTFields: a radical new approach to cancer treatment using electric fields," they state "inhibition of cell proliferation and accelerated cell death by TTFields are optimal at intensities of 1-5 V cm-1 and frequencies between 100 and 500 kHz, depending on the cell type—the mitotic spindle is best disrupted at 150 kHz in pancreatic cancer and NSCLC, and at 200 kHz in ovarian cancer and GBM. Mitosis in non-cancerous cells is typically disrupted at frequencies of about 50 kHz." For optimal outcomes, Novocure adds that TTFields should be applied for a minimum of 18 hours per day. In this sense, average daily usage of the device (i.e. treatment compliance) is a crucial component of clinical benefit."

SUMMARY

This disclosure refers to methods and devices for tissue stimulation with electromagnetic fields by means of frequency scanning, and, more specifically, to a first method for tissue stimulation with electric field by frequency variation, a second method for tissue stimulation with magnetic field by frequency variation, a third method that combines tissue stimulation with electric and magnetic fields by frequency variation, and a device for tissue stimulation with electromagnetic fields.

The first method for tissue stimulation with electromagnetic fields that comprises the following stages: a) applying an electric field stimulation to a tissue through an arrangement of electromagnetic transducers that receives an activation signal, the frequency of which varies from an initial tissue stimulation frequency ($f_{ie}$) to a final tissue stimulation frequency ($f_{fe}$), with increments or decrements in steps of the frequency delta ($\Delta f_e$) during a time delta ($\Delta t_e$); b) measuring the tissue impedance response to the stimulus of stage (a); c) establishing a reference level with the tissue impedance response measured in stage (b); d) establishing a tolerance (NT) to the reference level established in stage c); e) determining lower tissue stimulation frequencies ($f_{bx}$) as the point where the tissue impedance response falls below the tolerance (NT) established in stage (d); f) determining upper tissue stimulation frequencies ($f_{tx}$) as the point where the tissue impedance response returns to the tolerance (NT) established in stage (d); wherein the upper tissue stimulation frequencies ($f_{tx}$) are greater than the lower tissue stimulation frequencies ($f_{bx}$) and "x" is a natural number greater than or equal to 1.

The second method for tissue stimulation with electrical fields that comprises the following stage: a') applying a magnetic field stimulus to a tissue through an arrangement of electromagnetic transducers that receive an activation signal, the frequency of which varies from an initial tissue stimulation frequency ($f_{im}$) to a final tissue stimulation frequency ($f_{fm}$), with increments or decrements in steps of the frequency delta ($\Delta f_m$) during a time delta ($\Delta t_m$); b') measuring the tissue impedance response to the magnetic field stimulus through the electric field transducers of the arrangement of electromagnetic transducers; c') establishing a reference level with the tissue impedance response measured in stage (b'); d') establishing a tolerance (NT) to the reference level established in stage c'); e') determining lower tissue stimulation frequencies ($f_{bx}$) as the point where the tissue impedance response falls below the tolerance (NT) established in stage (d'); f') determining upper tissue stimulation frequencies ($f_{tx}$) as the point where the tissue impedance response returns to the tolerance (NT) established in stage (d'); wherein the upper tissue stimulation frequencies ($f_{tx}$) are greater than the lower tissue stimulation frequencies ($f_{bx}$) and "x" is a natural number greater than or equal to 1.

In addition, this disclosure includes other means for tissue stimulation with combinations of magnetic fields and electric fields with feedback for dynamically adjusting the electromagnetic stimulation signals.

The device for stimulating a tissue with electromagnetic fields, the device comprising: a computing unit; an external power source connected to the computing unit; a decoupling circuit connected to the external power source and to the computing unit; an arrangement of electromagnetic transducers connected to the computing unit and to the decoupling circuit; wherein the computing unit implements a method to generate an activation signals that receive the arrangement of the electromagnetic transducers through the decoupling circuit.

There is a long felt need for improving the efficiency of the tissue stimulation to avoid overstimulation and to adapt the stimulation according to each particular tissue. The methods of disclosed in the present document resolve this problem through the feedback of the tissue stimulation response and dynamically adjusting the stimulation signal.

BRIEF DESCRIPTION OF THE DRAWINGS

FIG. 5A shows an example of the frequency variation of a stimulation signal over time.

FIG. 5B shows an example of a sinusoidal-wave activation signal.

FIG. 5C shows an example of a square-wave activation signal.

FIG. 9A shows an example of tissue impedance response in band-stop shape with a frequency scan electromagnetic stimulation.

FIG. 9B shows an example of an approximate representation of the tissue impedance response in band-stop shape with a frequency scan electromagnetic stimulation.

FIG. 9C shows an example of tissue impedance response in low-pass shape of a frequency scan electromagnetic stimulation.

FIG. 9D shows an example of an approximate representation of the tissue impedance response in low-pass shape of a frequency scan electromagnetic stimulation.

FIG. 10A shows an example of tissue impedance response in band-stop shape with four bands of frequency scan electromagnetic stimulation.

FIG. 10B shows an example of an approximate representation of the tissue impedance response in band-stop shape with four bands of a frequency scan electromagnetic stimulation.

DETAILED DESCRIPTION

Figure 1:
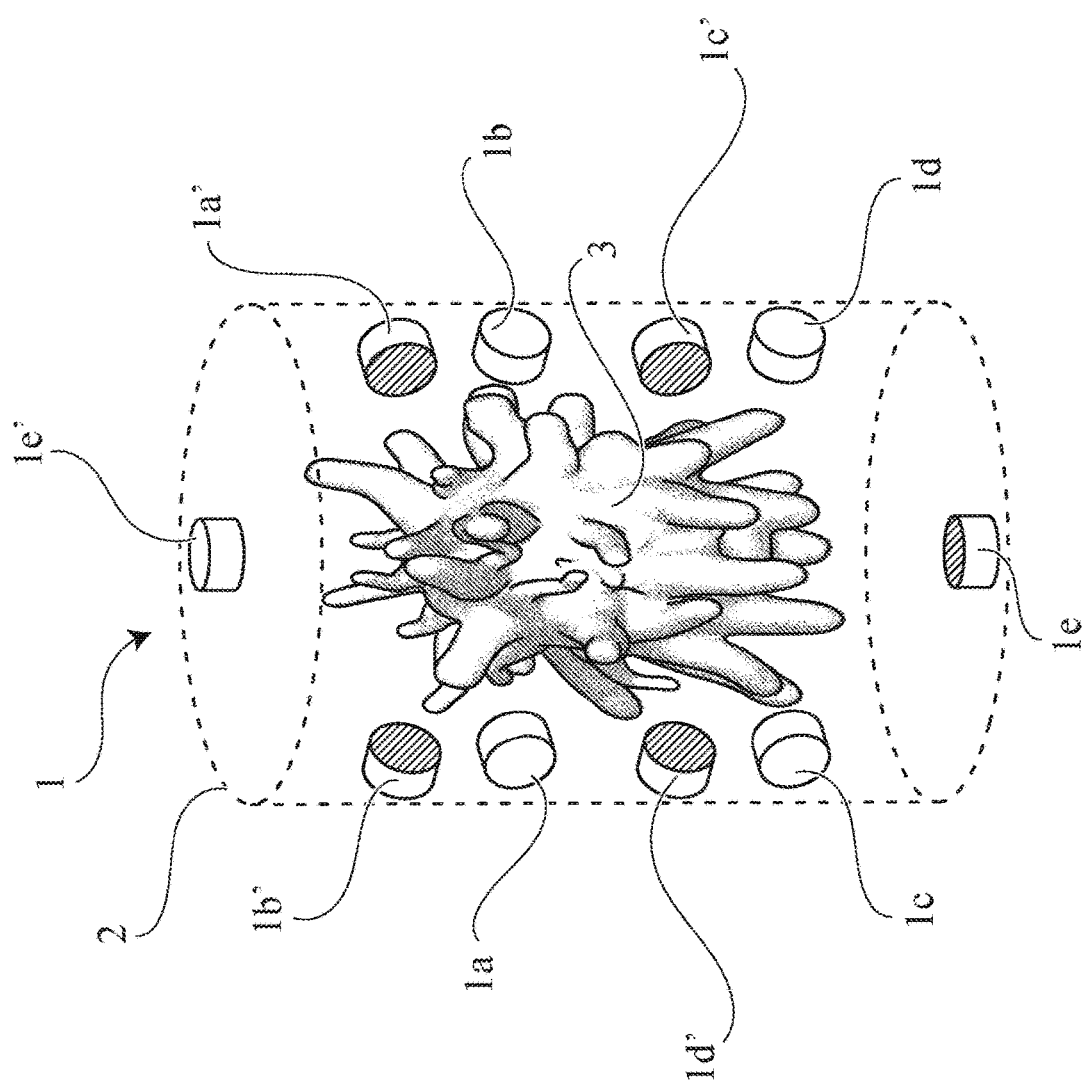
FIG. 1 shows an example of an arrangement of transducers over a volume that contains a tissue.

This disclosure unveils methods for frequency scan of electric and magnetic fields, or combinations of same, applied to a tissue and a device for electric and magnetic fields stimulation. The first method for frequency scan of electric and magnetic fields comprises tissue stimulation with electric fields that includes the following stages:

a) applying an electric field stimulus to a tissue through an arrangement of electromagnetic transducers that receives an activation signal, the frequency of which varies from an initial tissue stimulation frequency ($f_{ie}$) to a final tissue stimulation frequency ($f_{fe}$) with increments or decrements in steps of a frequency delta ($\Delta f_e$) during a time delta ($\Delta t_e$);

b) measuring the tissue impedance response to the stimulus of stage (a);

c) establishing a reference level with the tissue impedance response measured in stage (b);

d) establishing a tolerance (NT) to the reference level established in stage (c);

e) determining lower tissue stimulation frequencies ($f_{bx}$) as the point where the tissue impedance response falls below the tolerance (NT) established in stage (d);

f) determining upper tissue stimulation frequencies ($f_{tx}$) as the point where the tissue impedance response returns to the tolerance (NT) established in stage (d);

wherein the upper tissue stimulation frequencies ($f_{tx}$) are greater than the lower tissue stimulation frequencies ($f_{bx}$) and "x" is a natural number greater than or equal to 1.

Tissue refers to the biological tissues of living beings comprised of one or more cells, may be constituted by cells of only one class, all the same, or by various types of cells arranged in an orderly fashion to form an organ or an organism. The cited tissue may be healthy tissue, such as epithelial tissue, connective tissue, muscle tissue, muscular package, nerve tissue or combinations of these. The tissue may also be a tissue with a total or partial bio-chemical imbalance in healthy tissue, said bio-chemical imbalance in turn may correspond to benign tissue, neoplastic tissue, malignant neoplastic tissue or any cell out of homeostasis or in homeostasis. Also, tissue may refer to cells in vivo or prior to implantation said cells into an in vivo environment.

The tissue may come or be from animals including, without limitation: mammals, avian species, including chickens, turkeys, geese and ducks; fish, crustacean species (shrimp, lobsters, crayfish); and reptiles such as crocodiles and alligators. The term "mammal" as used herein refers to any mammal classified as a mammal, including humans, non-human primates, such as cynomolgus monkey, chimpanzees, baboon and gorilla; domestic and farm animals including equine species, bovine species, swine species, caprine species, canine species, feline species, ovine species, rabbits, llamas; ungulates, such as bovine, ovine, porcine, equine, caprine; canine, feline, murine, rabbit; and rodents such as guinea pigs, hamsters and rats.

The stimulation of a biological tissue refers to administering energy to said biological tissue in order to induce certain changes in the characteristics of said biological tissue such as tissue impedance response, tissue vascularization, tissue temperature, tissue health, tissue growth rate, among others.

Figure 17:
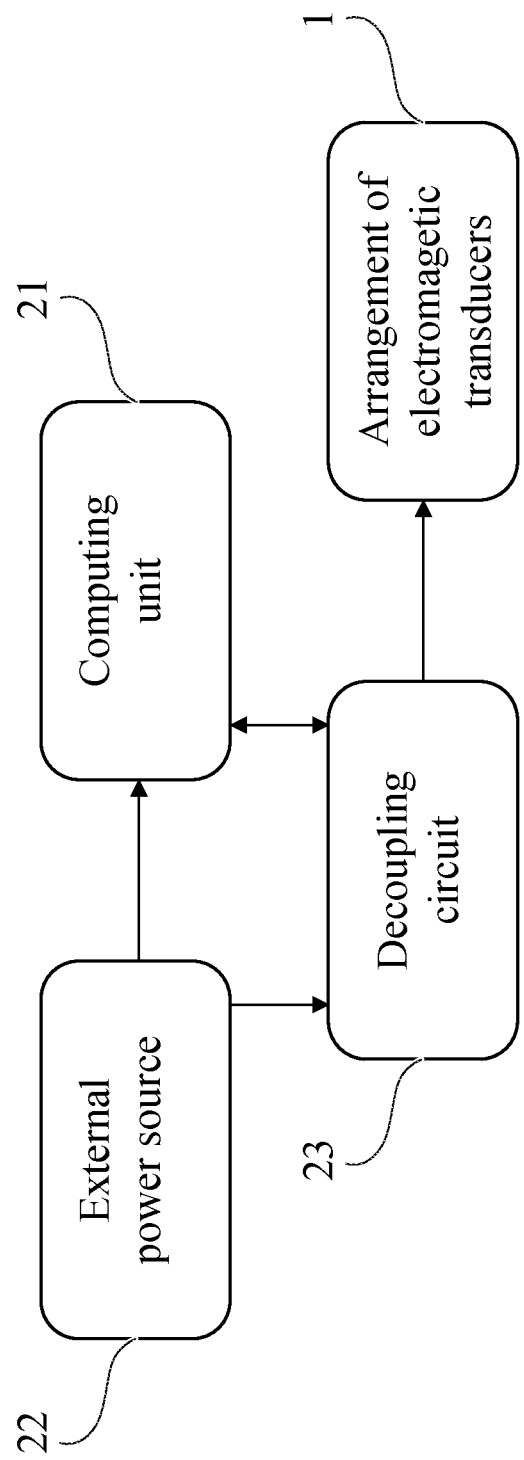
FIG. 17 shows a block diagram of an example of a tissue stimulating device of this disclosure.

In reference to FIG. 17 an example of a tissue stimulating device of the present disclosure is shown, the tissue stimulating device comprises a computing unit (21), an external power source (22) connected to the computing unit (21), a decoupling circuit (23) connected to the external power source (22) and to the computing unit (21), an arrangement of electromagnetic transducers (1) connected to the computing unit (21) and to the decoupling circuit (23); the computing unit (21) implements the method for tissue stimulation with a frequency scan electric field, the method for tissue stimulation with a frequency scan magnetic field, and methods that combine stimulation with electrical fields and magnetic fields and may be configured with the tissue stimulating device in order to generate activation signals that receive the electromagnetic field transducers, electric field or magnetic field through the decoupling circuit (23).

Said control system may also be understood as a tissue stimulating device, a device for stimulating a tissue with electromagnetic fields or simply a device for stimulating a tissue.

Figure 18:
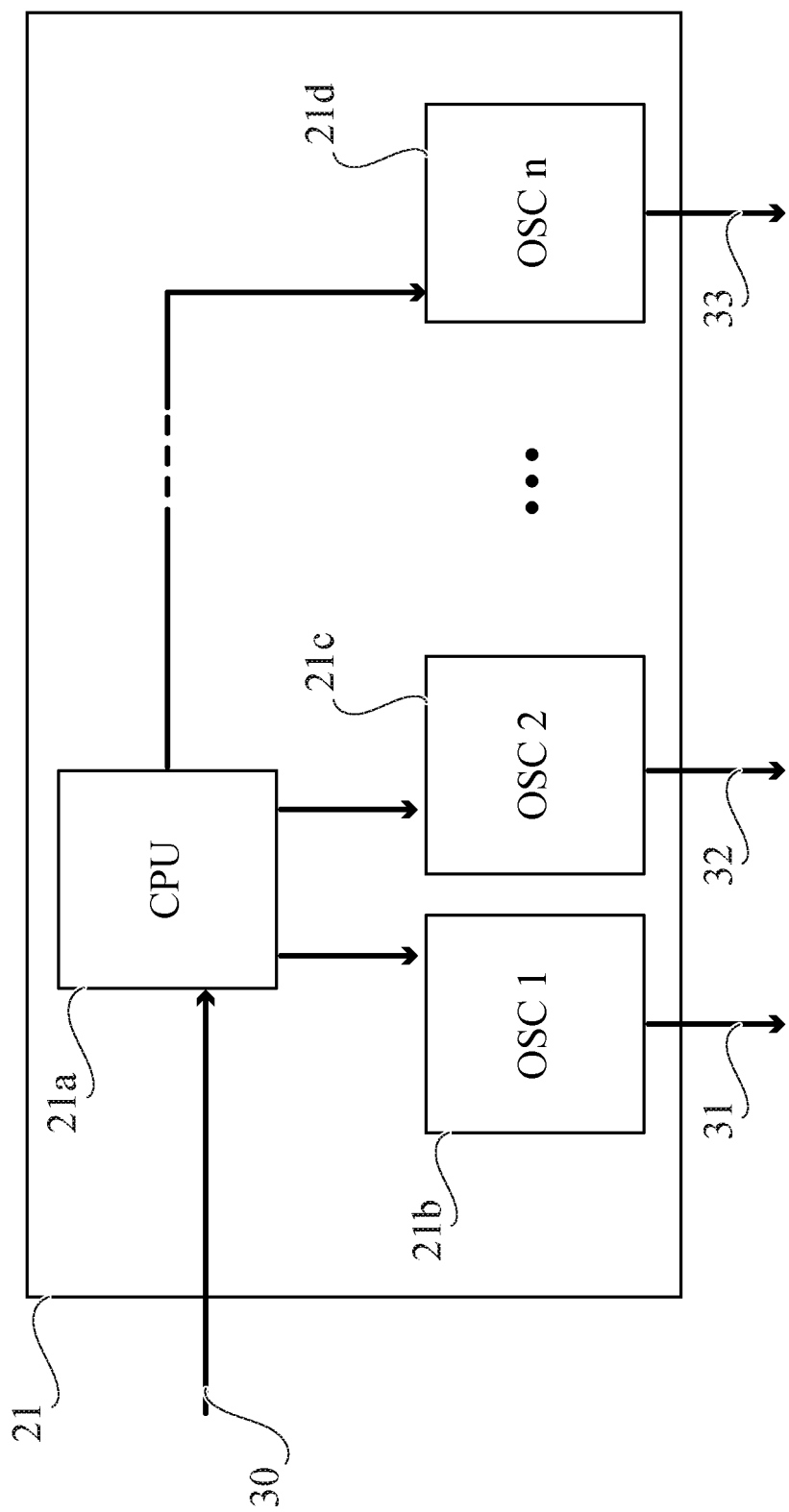
FIG. 18 shows a block diagram of an example of a special purpose computing unit of a tissue stimulating device of this disclosure.

In reference to FIG. 18, an example of the computing unit (21) being a special purpose computing unit which comprises a central processor unit (CPU) (21 a) connected to oscillators from a first OSC 1 (21 b), a second oscillator OSC 2 (21 c) to an oscillator OSC n (21 d) each oscillator having activation signal outputs (31, 32 and 33), wherein n is a natural number equal or greater than zero, according to this the computing unit (21) may have a maximum of n activation signal outputs. Activation signal outputs are also named as channels.

Optionally, the activation signal output (31, 32 and 33) of each oscillator is connected to the arrangement of electromagnetic transducers (1) directly or through a decoupling circuit (23). Alternatively, the CPU (21a) is also connected to a peripheral device selected among others, from storage devices such as a memory unit, a database and a hard drive, input devices such as a keyboard, a camera, a touchscreen display, and a scanner, output devices such as a display and a printer.

In another example of the tissue stimulating device the oscillators are replaced by signals generators.

Optionally, the parameters of each activation signal such as frequency, phase, amplitude, duty cycle, can be modified by instructions of a remote computing unit, by a user through an HID connected to the tissue stimulating device.

The computing unit (21) of the tissue stimulating device may use feedback (30), for example, a tissue impedance response feedback in order to dynamically adjust the activation signal outputs (31, 32 and 33) which are received by the transducers and applied to the tissue to stimulate it.

Feedback (30) is a mechanism by which a certain portion of the output of a system is redirected back to the input, for the purpose of controlling its behavior. For example, when stimulating the tissue with electrical fields, or magnetic fields or both fields, there may be a variation in tissue impedance response, feedback of the tissue impedance response can be used by employing electric field transducers, said feedback making it possible to perceive variations in the tissue impedance response and to dynamically adjust the activation signal.

Alternatively, feedback is not limited to obtaining the tissue impedance response to the tissue stimulus. Feedback may incorporate, for example, measuring the temperature in order to determine tissue fatigue, images of the tissue surface in order to determine tissue vascularization, tissue impedance response measurements, or combinations of these.

When stimulating the tissue with electric fields, or magnetic fields, or both fields, there may be increments of temperature on the surface of the tissue, a temperature sensor or temperature measuring device may be used to perceive temperature variations and to dynamically adjust the stimulus activation signal of electrical fields, magnetic fields, or both fields, in order to, for example, avoid lesions on the tissue due to overheating.

In order to understand this disclosure, a computing unit is a device that processes data, for example, microcontrollers, microprocessors, DSCs (Digital Signal Controllers), FPGAs (Field Programmable Gate Arrays), CPLDs (Complex Programmable Logic Devices), ASICs (Application Specific Integrated Circuits), SoCs (Systems on Chip), PSoCs (Programmable Systems on Chip), computers, servers, tablets, cellular telephones, smart phones and computer units known to those skilled in the art, and combinations of these. This computing unit may include a storage device, display device and/or a Human Interface Device (HID), may be or include a special purpose computing unit programmed to run the method of this disclosure.

A storage device includes, without limiting, RAM memory (cache memory, SRAM, DRAM, DDR), ROM memory (Flash, cache, HDD, SSD, EPROM, EEPROM, removable memory ROM (SD (miniSD, microSD, etc), MMC (MultiMedia Card), Compact Flash, SMC (Smart Media Card), SDC (Secure Digital Card), MS (Memory Stick), among others)), CD-ROM, Digital Versatile Disc (DVD) or other optical storage, magnetic cassettes, magnetic tapes, storage or any other means that can be used to store information and which can be accessed by a computer unit, among others known to those skilled in the art, and combinations of these. The storage device have memory registers, in which instructions, data structures and software modules are stored.

A display includes, without limiting, monitors and is anything capable of being connected to a computing unit and displaying its output. CRT monitor, flat panel display, Liquid Crystal D Liquid Crystal Display (LCD), active matrix LCD, passive matrix LCD, LED displays, display projectors, TV (4KTV, HDTV, Plasma TV, Smart TV), OLED displays, AMOLED Displays, Quantum dot (QD) displays, segments displays, among other devices capable of showing data to a user, known to those skilled in the art, and combinations of these.

A HID includes, without limiting, keyboard, mouse, trackball, touchpad, pointing stick, joystick, touch screen, among other devices capable of allowing a user to input data into the computing unit of the tissue stimulating device, known to those skilled in the art, and combinations of these.

The decoupling circuit makes it possible to electrically decouple the external power source from the arrangement of electromagnetic transducers, said circuit may be based on optocouplers, relays, operational amplifiers, resistors, condensers, transformers, combination diodes of these and other electronic elements for electrically decoupling two electrical circuits or elements.

The external power source makes it possible to provide the electric power required for operation of the arrangement of electromagnetic transducers and may be a device capable of maintaining a power differential between two or more terminals such as an alternating current power source, a continuous current power source, batteries, photovoltaic power source, thermoelectric power source, among other devices capable of maintaining a voltage between two or more terminals known to those skilled in the art, or combinations of these.

The activation signal received by the transducers of the arrangement of electromagnetic transducers (1), electrical field transducers, or magnetic field transducers may be a signal selected between a direct current or alternating current signal, a pulsed signal, a train of alternating or non-alternating impulsive signals, a square wave signal with variation of the duty cycle, triangular wave signal, sawtooth wave signal, modulated by amplitude (AM), modulated by frequency (FM), modulated by phase (PM), modulated by pulse positions (PPM), modulated by pulse width (PWM), and combinations of these. These signals are generated by a computing unit or by a signals generator or combinations of these, according to programs and feedback.

The programs cited by this disclosure correspond to information, coded or not, in a computing unit and which modify all of the parameters of the activation signal that activates the arrangement transducers (1).

The signals generators can be selected from the group of professional wave generators, integrated circuits synthesizers DDS (Direct Digital Synthesizer)/DAC (Digital to Analog Conversion), NCO (Numerically Controlled Oscillator), arrays of operational amplifiers in wave generator configuration, bistable oscillator circuits and combinations of the above. The signal generator may also be named as wave generator.

Additionally, the computing unit (21) makes it possible for one or more activation signals to be applied to each transducer at a determined time, sequentially, out of phase in relation to the other activation signal or to various stimulation signals, randomly or according to a program established for each one of the transducers.

The activation signal that activates the transducers of the arrangement of electromagnetic transducers (1) may be understood as electromagnetic stimulation signal, electrical stimulation signal when the prevailing phenomenon is from the electrical field, magnetic stimulation signal when the prevailing phenomenon is from the magnetic field.

In order to activate the electrical field transducers, the activation signal may be selected, among other things, from direct current or alternating current signal, pulsed signal, a train of alternating or non-alternating impulsive signals, square wave signal with variation of the duty cycle, triangular wave signal, sawtooth wave signal, modulated by amplitude (AM), modulated by frequency (FM), modulated by phase (PM), modulated by pulse positions (PPM), modulated by pulse width (PWM), and combinations of these.

In stage a) of the method of this disclosure, the method initiates with stimulation of the tissue applying a signal with a determined frequency for a specific period of time which can be limited by a user or can be programmed in a computing unit. For example, the method can initiate with a $f_{ie}$ of 1 Hz applied for a $\Delta t_e$ of 1 second, incrementing the frequency $f_{ie}$ a $\Delta f_e$ equal to 1 Hz, applying the new $f_{ie}$ of 2 Hz during a $\Delta t_e$ of 1 second, and continuing increments with the same $\Delta f_e$, applying the new $f_{ie}$ during a $\Delta t_e$ of 1 second.

An arrangement of electromagnetic transducers may be a set of "n" electrical field transducers or magnetic field transducers, or a combination of these, with "n" being a natural number greater than or equal to 1.

Said electromagnetic transducers can be designated as electromagnetic field transducers, they can be electrical field transducers or magnetic field transducers or can be configured by a combination of electrical field transducers and magnetic field transducers. Magnetic field transducers may also be designated as magnetic transducers and electric field transducers may also be designated as electrical transducers. In the case of the electrical field being the prevailing phenomenon, it is understood that said electromagnetic transducers are electrical field transducers, at the same time, when the prevailing phenomenon is the magnetic field, it is understood that the electromagnetic transducers are magnetic field transducers.

The transducers of the arrangement of electromagnetic transducers have an active face in different shapes which can be selected, among others, from the group of geometric figures such as squares, rectangles, circles, ovals, concentric rings and combinations of these, such that they cover different areas of the external surface of a volume that contains the tissue of interest.

The active face of a transducer is the surface of the transducer through which the electrical field signal, magnetic field signal, or electromagnetic field signal has greater intensity.

The electrical field transducers are selected, among others, from the group that consists of engines, electrodes, photoelectric transducers, electrical induction actuators, conducting plates that generate electrical fields, antennas, or combinations of these. The magnetic field transducers are selected, among others, from the group that consists of engines, electrodes, magnetic induction actuators, magnetic field generating coils with or without a core, electromagnets, antennas and combinations of these.

In reference to FIG. 1, for example, an arrangement of electromagnetic transducers (1) is placed on the surface of a volume (2), which arrangement comprises from an electromagnetic transducer (1a) to an electromagnetic transducer (1e'), which, in the illustrated example, comprises pairs of transducers, a first pair of electromagnetic transducers comprised of a transducer (1a) and a transducer (1a'), a second pair of electromagnetic transducers, comprised by a transducer (1b) and a transducer (1b'), a third pair of electromagnetic transducers comprised of a transducer (1c) and a transducer (1c'), a fourth pair of electromagnetic transducers comprised of a transducer (1d) and a transducer (1d'), a fifth pair of electromagnetic transducers comprised of a transducer (1e) and a transducer (1e') Each pair of transducers face each other and are each oriented with their active face such that it targets the interior of the volume (2) that contains a tissue (3) of interest. Optionally, the active faces of the transducers are directed toward the tissue (3).

In addition, the arrangement (1) optionally meets a condition of orthogonality in that a plane parallel to any of the surfaces of the active faces of the first pair of transducers is orthogonal to another plane parallel to any of the surfaces of the active faces of the second, third, fourth and fifth pair of transducers, and in addition, any plane parallel to the surfaces of the active faces of the second pair of transducers is orthogonal to any other plane parallel to any of the surfaces of the active faces of the third, fourth and fifth pair of transducers, and additionally, any plane parallel to the surfaces of the active faces of the third pair of transducers is orthogonal to any other plane parallel to any of the surfaces of the active faces of the fourth and fifth pair of transducers, and also any plane parallel to the surfaces of the active faces of the fourth pair of transducers is orthogonal to any other plane parallel to any of the surfaces of the active faces of the fifth pair of transducers, and in addition, projections of the planes of the active faces pointed toward the tissue cover the maximum surface possible of said tissue, with this configuration ensuring optimum stimulation of the tissue.

It may also be possible that the transducers that comprise each pair of transducers are not completely aligned or parallel to each other, or do not preserve the condition of orthogonality of the transducers described in the previous paragraph, may also succeed in stimulating the tissue (3).

In one example of this disclosure, the active face of the electrical field transducers in the arrangement of electromagnetic transducers (1) is in contact with the external surface of the tissue (3). In this way, less electrical power is required for the operation of the electrical field transducers in comparison with the other alternative where the electrical field transducers are located a determined distance from the external surface of the tissue (3).

In another example, the active face of the transducers that comprise the arrangement of electromagnetic transducers (1) is separated by a determined distance from the external surface of the tissue (3) (necessary, for example, when it is not possible to make physical contact with the external surface of the tissue). In this way, more electrical power may be required for the operation of the electrical field transducers in comparison with the alternative where the electrical field transducers are in contact with the external surface of the tissue (3).

Alternatively, the active face of the transducers that comprise the arrangement of electromagnetic transducers (1) is separated by a determined distance from the external surface of the tissue (3) and a second group of transducers of the arrangement of electromagnetic transducers (1) is in contact with the external surface of the tissue (3)

This mixed configuration of the positioning of the transducers makes it possible, for example, to efficiently reach the tissue (3) found in the volume (2) where the surface of said tissue (3) varies such that some areas tolerate physical contact with the active face of the transducer and other areas are difficult to access or do not tolerate such physical contact.

Optionally, in stage (a), the active face of at least one of the electrical field transducers in the arrangement of electromagnetic transducers (1) is in contact with the external surface of the tissue (3).

Projections of the planes of the active faces of the transducers are arranged in the direction of the tissue (3) and cover the maximum possible surface area of said tissue (3), with this configuration ensuring optimum stimulation of the tissue.

In addition, it is possible that the transducers are not completely aligned or parallel to each other.

The intensity and direction parameters of a vector of the electrical field toward the interior of the volume (2) depend on the disposition of the transducers around the volume (2) that contains the tissue (3). For example, with an arrangement of electrical field transducers, if the active face is in contact with the surface of the volume (2), then the intensity of the electrical field will be between 2 V/cm and 5 V/cm. If, on the other hand, the electrical field transducers are located a defined distance from the surface, then the intensity value of the electrical field will be between 330 V/cm and 20 kV/cm for distances between 0.01 cm and 50 cm, and optionally between 0.01 cm and 4 cm.

Alternatively, the intensity value of the electrical field for transducers having their active face in contact with the surface of the tissue may be selected among a range 2 V/cm to 5 V/cm, from 2.1 V/cm to 4.9 V/cm, from 2.2 V/cm to 4.8 V/cm, from 2.3 V/cm to 4.7 V/cm, from 2.4 V/cm to 4.6 V/cm, from 2.5 V/cm to 4.5 V/cm, from 2.6 V/cm to 4.4 V/cm, from 2.7 V/cm to 4.3 V/cm, from 2.8 V/cm to 4.2 V/cm, from 2.9 V/cm to 4.1 V/cm, from 3 V/cm to 4 V/cm, from 3.1 V/cm to 3.9 V/cm, from 3.2 V/cm to 3.8 V/cm, from 3.3 V/cm to 3.7 V/cm, from 3.4 V/cm to 3.6 V/cm, from 2.2 V/cm to 5 V/cm, from 2.4 V/cm to 5 V/cm, from 2.6 V/cm to 5 V/cm, from 2.8 V/cm to 5 V/cm, from 3 V/cm to 5 V/cm, from 3.2 V/cm to 5 V/cm, from 3.4 V/cm to 5 V/cm, from 3.6 V/cm to 5 V/cm, from 3.8 V/cm to 5 V/cm, from 4 V/cm to 5 V/cm, from 4.2 V/cm to 5 V/cm, from 4.4 V/cm to 5 V/cm, from 4.6 V/cm to 5 V/cm, from 4.8 V/cm to 5 V/cm, from 2 V/cm to 4.8 V/cm, from 2 V/cm to 4.6 V/cm, from 2 V/cm to 4.4 V/cm, from 2 V/cm to 4.2 V/cm, from 2 V/cm to 4 V/cm, from 2 V/cm to 3.8 V/cm, from 2 V/cm to 3.6 V/cm, from 2 V/cm to 3.4 V/cm, from 2 V/cm to 3.2 V/cm, from 2 V/cm to 3 V/cm, from 2 V/cm to 2.8 V/cm, from 2 V/cm to 2.6 V/cm, from 2 V/cm to 2.4 V/cm, from 2 V/cm to 2.2 V/cm, from 2.2 V/cm to 2.4 V/cm, from 2.4 V/cm to 2.6 V/cm, from 2.6 V/cm to 2.8 V/cm, from 2.8 V/cm to 3 V/cm, from 3 V/cm to 3.2 V/cm, from 3.2 V/cm to 3.4 V/cm, from 3.4 V/cm to 3.6 V/cm, from 3.6 V/cm to 3.8 V/cm, from 3.8 V/cm to 4 V/cm, from 4 V/cm to 4.2 V/cm, from 4.2 V/cm to 4.4 V/cm, from 4.4 V/cm to 4.6 V/cm, from 4.6 V/cm to 4.8 V/cm, from 4.8 V/cm to 5 V/cm.

Optionally, the intensity value of the electrical field for transducers located a defined distance from the surface of the tissue may be selected among a range from 0.33 kV/cm to 20 kV/cm, from 0.83 kV/cm to 19.5 kV/cm, from 1.33 kV/cm to 19 kV/cm, from 1.83 kV/cm to 18.5 kV/cm, from 2.33 kV/cm to 18 kV/cm, from 2.83 kV/cm to 17.5 kV/cm, from 3.33 kV/cm to 17 kV/cm, from 3.83 kV/cm to 16.5 kV/cm, from 4.33 kV/cm to 16 kV/cm, from 4.83 kV/cm to 15.5 kV/cm, from 5.33 kV/cm to 15 kV/cm, from 5.83 kV/cm to 14.5 kV/cm, from 6.33 kV/cm to 14 kV/cm, from 6.83 kV/cm to 13.5 kV/cm, from 7.33 kV/cm to 13 kV/cm, from 7.83 kV/cm to 12.5 kV/cm, from 8.33 kV/cm to 12 kV/cm, from 8.83 kV/cm to 11.5 kV/cm, from 9.33 kV/cm to 11 kV/cm, from 9.83 kV/cm to 10.5 kV/cm, from 1.33 kV/cm to 20 kV/cm, from 2.33 kV/cm to 20 kV/cm, from 3.33 kV/cm to 20 kV/cm, from 4.33 kV/cm to 20 kV/cm, from 5.33 kV/cm to 20 kV/cm, from 6.33 kV/cm to 20 kV/cm, from 7.33 kV/cm to 20 kV/cm, from 8.33 kV/cm to 20 kV/cm, from 9.33 kV/cm to 20 kV/cm, from 10.33 kV/cm to 20 kV/cm, from 11.33 kV/cm to 20 kV/cm, from 12.33 kV/cm to 20 kV/cm, from 13.33 kV/cm to 20 kV/cm, from 14.33 kV/cm to 20 kV/cm, from 15.33 kV/cm to 20 kV/cm, from 16.33 kV/cm to 20 kV/cm, from 17.33 kV/cm to 20 kV/cm, from 18.33 kV/cm to 20 kV/cm, from 19.33 kV/cm to 20 kV/cm, from 0.33 kV/cm to 19 kV/cm, from 0.33 kV/cm to 18 kV/cm, from 0.33 kV/cm to 17 kV/cm, from 0.33 kV/cm to 16 kV/cm, from 0.33 kV/cm to 15 kV/cm, from 0.33 kV/cm to 14 kV/cm, from 0.33 kV/cm to 13 kV/cm, from 0.33 kV/cm to 12 kV/cm, from 0.33 kV/cm to 11 kV/cm, from 0.33 kV/cm to 10 kV/cm, from 0.33 kV/cm to 9 kV/cm, from 0.33 kV/cm to 8 kV/cm, from 0.33 kV/cm to 7 kV/cm, from 0.33 kV/cm to 6 kV/cm, from 0.33 kV/cm to 5 kV/cm, from 0.33 kV/cm to 4 kV/cm, from 0.33 kV/cm to 3 kV/cm, from 0.33 kV/cm to 2 kV/cm, from 0.33 kV/cm to 1 kV/cm, from 1.33 kV/cm to 2.33 kV/cm, from 2.33 kV/cm to 3.33 kV/cm, from 3.33 kV/cm to 4.33 kV/cm, from 4.33 kV/cm to 5.33 kV/cm, from 5.33 kV/cm to 6.33 kV/cm, from 6.33 kV/cm to 7.33 kV/cm, from 7.33 kV/cm to 8.33 kV/cm, from 8.33 kV/cm to 9.33 kV/cm, from 9.33 kV/cm to 10.33 kV/cm, from 10.33 kV/cm to 11.33 kV/cm, from 11.33 kV/cm to 12.33 kV/cm, from 12.33 kV/cm to 13.33 kV/cm, from 13.33 kV/cm to 14.33 kV/cm, from 14.33 kV/cm to 15.33 kV/cm, from 15.33 kV/cm to 16.33 kV/cm, from 16.33 kV/cm to 17.33 kV/cm, from 17.33 kV/cm to 18.33 kV/cm, from 18.33 kV/cm to 19.33 kV/cm, from 19.33 kV/cm to 20 kV/cm.

Alternatively, transducers may be located a distance from the surface of the tissue a distance selected among a range from 0.01 cm to 50 cm, from 2 cm to 48 cm, from 4 cm to 46 cm, from 6 cm to 44 cm, from 8 cm to 42 cm, from 10 cm to 40 cm, from 12 cm to 38 cm, from 14 cm to 36 cm, from 16 cm to 34 cm, from 18 cm to 32 cm, from 20 cm to 30 cm, from 22 cm to 28 cm, from 24 cm to 26 cm, from 5 cm to 50 cm, from 10 cm to 50 cm, from 15 cm to 50 cm, from 20 cm to 50 cm, from 25 cm to 50 cm, from 30 cm to 50 cm, from 35 cm to 50 cm, from 40 cm to 50 cm, from 45 cm to 50 cm, from 0.01 cm to 45 cm, from 0.01 cm to 40 cm, from 0.01 cm to 35 cm, from 0.01 cm to 30 cm, from 0.01 cm to 25 cm, from 0.01 cm to 20 cm, from 0.01 cm to 15 cm, from 0.01 cm to 10 cm, from 0.01 cm to 5 cm, from 5 cm to 10 cm, from 10 cm to 15 cm, from 15 cm to 20 cm, from 20 cm to 25 cm, from 25 cm to 30 cm, from 30 cm to 35 cm, from 35 cm to 40 cm, from 40 cm to 45 cm, from 45 cm to 50 cm.

In another example of the disclosure, in stage (a), the arrangement of electromagnetic transducers (1) has at least two electrical field transducers, and at least two of said transducers activate simultaneously by means of a frequency scan for a determined period of time.

Alternatively, the electromagnetic transducers of the arrangement (1) are disposed over a frame (4) which encloses the volume (2) and the purpose of which is to provide a support structure for the electrical field transducers that are disposed with their active face pointing toward the tissue of interest. The frame (4) also can be used to change the shape of the surface of the volume (2) in order to obtain a plane surface that will make it possible to adjust the position of the electrical field transducers such that an optimal intensity of the electrical field is obtained for stimulation of the tissue (3). The frame (4) can be supported over the same tissue or be mechanically supported on a fixed or movable base. The type of frame (4) can be chosen from the group comprised of shirts, vests, gloves, helmets, glasses, braces, stockings, boots, shoes, scarves, collars, and other structures that provide support to the transducers and combinations of these. In addition, the frame (4) can cover the volume (2) either totally or partially.

Optionally, the base on which the frame (4) is set can be movable in order to make it possible to move the arrangement (1) in relation to the surface of the volume (2) and thus be able to reach different volumes from distinct external points and to vary the vector of the electrical field.

Figure 2B:
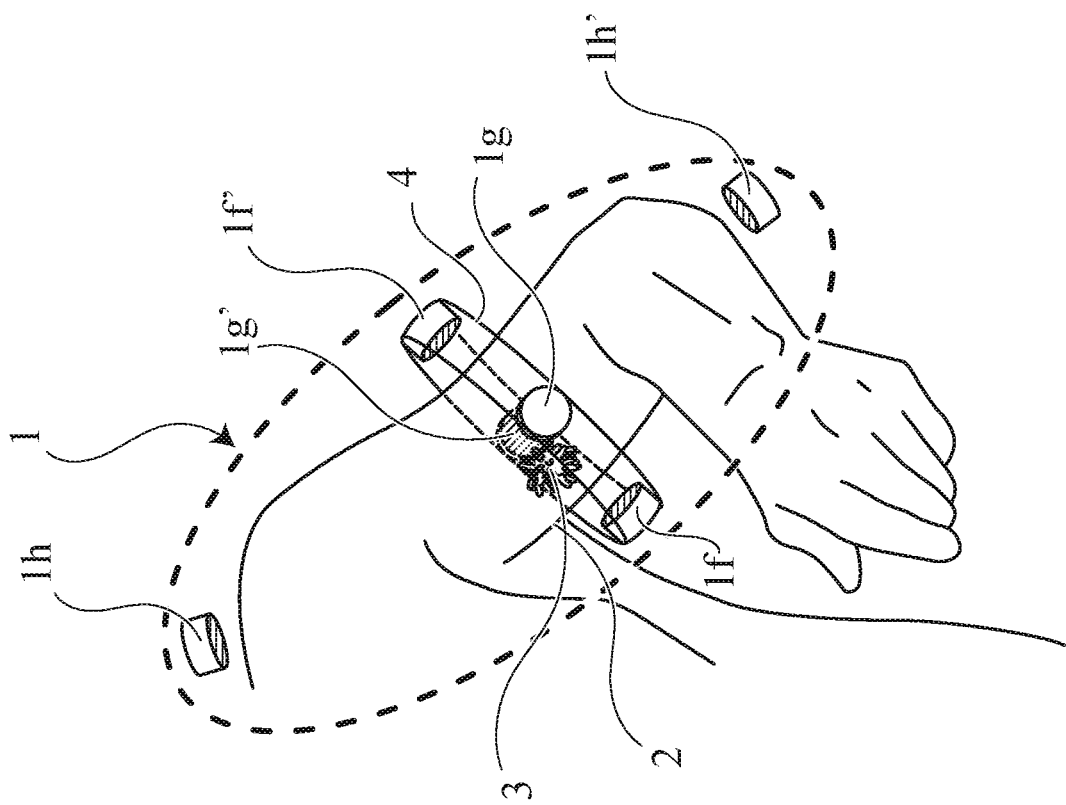
FIG. 2B shows an example of the placement of an arrangement of electromagnetic transducers without contact and targeting an arm tissue of an individual.
Figure 2A:
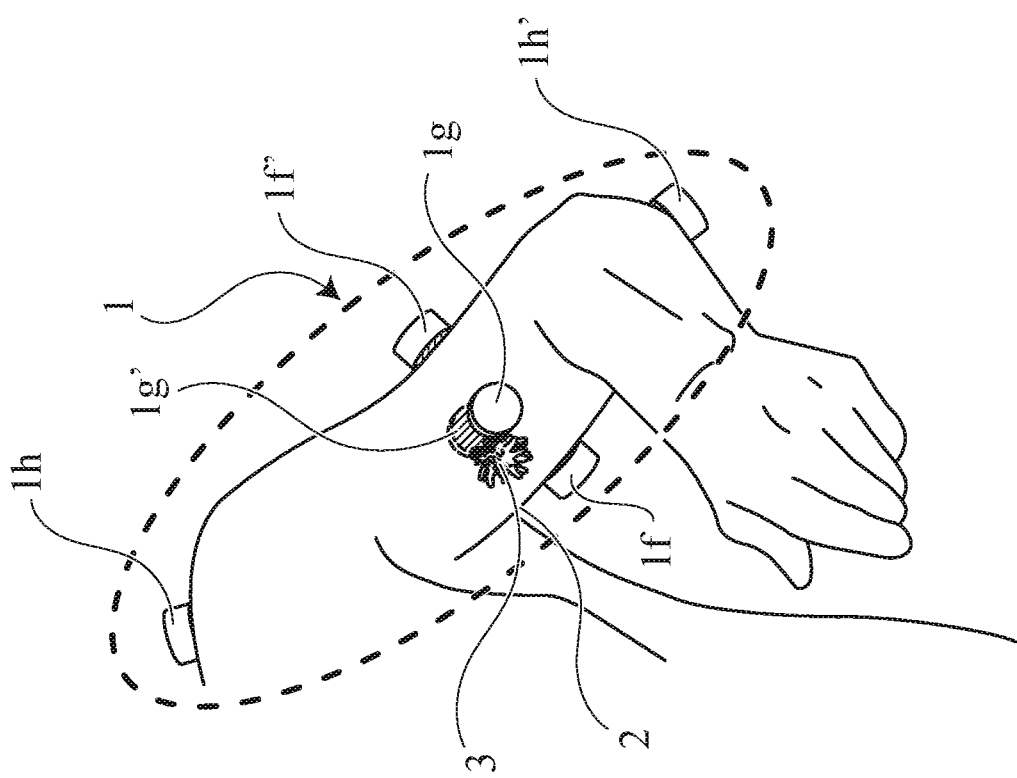
FIG. 2A shows an example of the placement of an arrangement of electromagnetic transducers in contact and targeting an arm tissue of an individual.

FIG. 2A illustrates the disposition of an arrangement of electromagnetic transducers (1) over a volume (2) which consists of the arm of an individual. In the interior of the arm is a tissue (3) which it is desired to stimulate electromagnetically. Said arrangement of electromagnetic transducers (1) comprises two groups of transducers as detailed below:

A first group of transducers comprised by two pairs of electromagnetic transducers. A first pair of electromagnetic transducers: a transducer (1f) and a transducer (1f), a second pair of electromagnetic transducers: a transducer (1g) and a transducer (1g'), the first pair and the second pair of electromagnetic transducers are disposed radially around the humerus with their active faces in contact with the surface of the skin.

A second group of transducers comprised by a pair of electromagnetic transducers: a transducer (1h) and a transducer (1h'), said pair of electromagnetic transducers is disposed over a plane normal to the axis of the humerus, the active face of the transducer (1h) over the shoulder and in contact with the skin, and the active face of the transducer (1h') over the elbow and in contact with the skin.

Each pair of transducers is disposed such that the active faces of the transducers that comprise said pair partially face each other, are aligned with their active faces in the direction of the position of the tissue (3) and with their active faces in contact with the skin.

In addition, the arrangement (1) optionally meets a condition of orthogonality in that a plane parallel to any of the surfaces of the active faces of the first pair of transducers is orthogonal to another plane parallel to any of the surfaces of the active faces of the second, and third pair of transducers, and in addition, any plane parallel to the surfaces of the active faces of the second pair of transducers is orthogonal to any other plane parallel to any of the surfaces of the active faces of the first and third pair of transducers, and in addition, projections of the planes of the active faces pointed toward the tissue cover the maximum surface possible of said tissue, with this configuration ensuring optimum stimulation of the tissue.

It may also be possible that the transducers that comprise each pair of transducers are not completely aligned or parallel to each other, or do not preserve the condition of orthogonality of the transducers described in the previous paragraph, may also succeed in stimulating the tissue (3).

There are various diagnostic tools for learning the location of the tissue (3), for example: magnetic resonance imaging, computerized tomography, PET (Positron Emission Tomography) scanning, x-rays, Doppler echography, electrocardiograms, diagnosis by palpation, marking with an arrow, among others.

It may also be possible to learn the location of the tissue (3) using a measurement of tissue impedance response.

FIG. 2B illustrates a similar disposition of the transducers, but where the active faces of the transducers are a distance of between 0.01 cm and 50 cm from the surface of the skin of the individual, supported on a frame (4), and optionally between 0.01 cm and 4 cm.

Figure 3A:
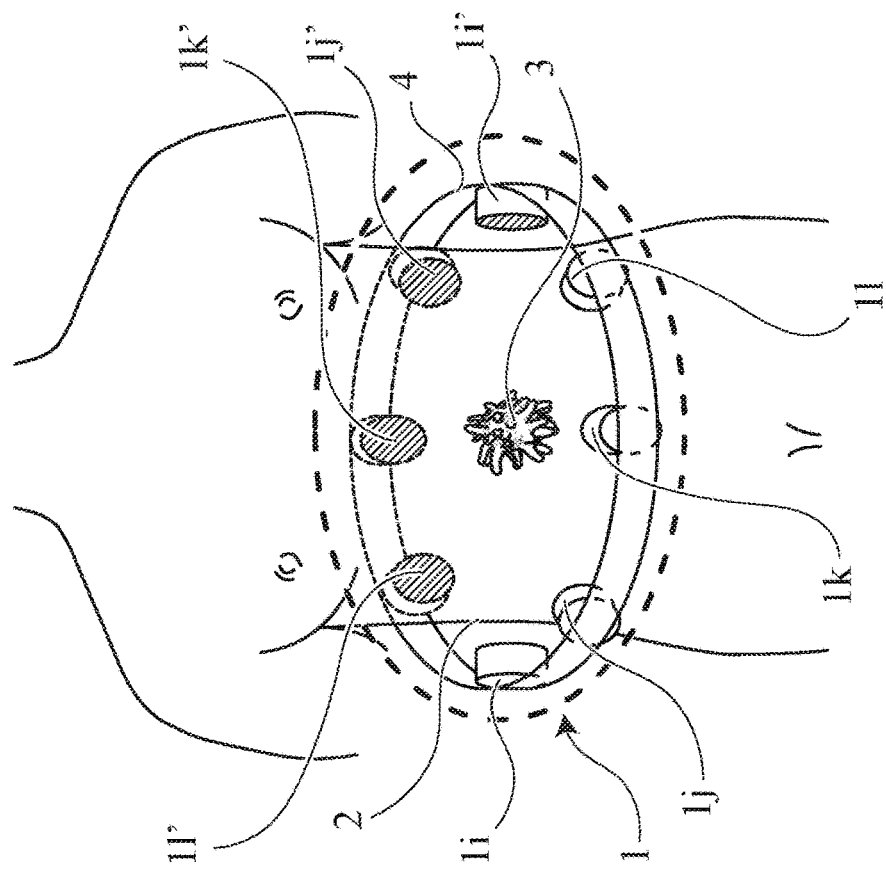
FIG. 3A shows an example of the placement of an arrangement of electromagnetic transducers in contact and targeting a tissue in the abdominal area of an individual.

FIG. 3A illustrates the disposition of an arrangement of electromagnetic transducers (1) over a volume (2) which consists of the abdomen of an individual. In the interior of the abdomen is a tissue (3) which it is desired to stimulate electromagnetically. Said arrangement of electromagnetic transducers (1) comprises five groups of transducers as detailed below:

A first pair of transducers: a transducer (1i) and a transducer (1i'), a second pair of transducers: a transducer (1j) and a transducer (1j'), a third pair of transducers: a transducer (1k) and a transducer (1k'), a fourth pair of transducers: a transducer (1l) and a transducer (1l').

Said pairs of transducers are disposed radially around an axis parallel to the spinal column, over the abdominal and dorsal area such that the active faces of the transducers face each other and in the direction of the position of the tissue (3) and with their active faces in contact with the skin.

Projections of the planes of the active faces of the transducers are arranged in the direction of the tissue and cover the maximum possible surface area of said tissue, with this configuration ensuring optimum stimulation of the tissue.

In addition, it is possible that the transducers that comprise each pair are not completely aligned or parallel to each other.

Figure 3B:
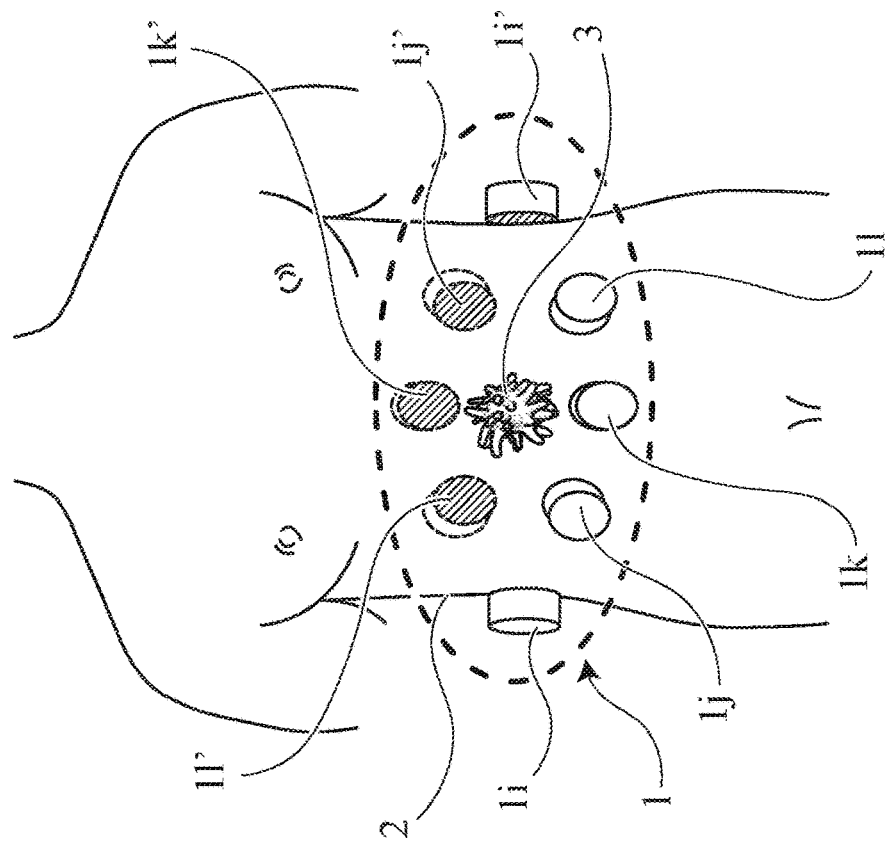
FIG. 3B shows an example of the placement of an arrangement of electromagnetic transducers without contact and targeting a tissue in the abdominal area of an individual.

FIG. 3B illustrates a similar disposition of the transducers, but where the active faces of the transducers are a distance of between 0.01 cm and 50 cm from the surface of the skin in the individual, supported on a frame (4), and optionally between 0.01 cm and 4 cm.

Figure 4A:
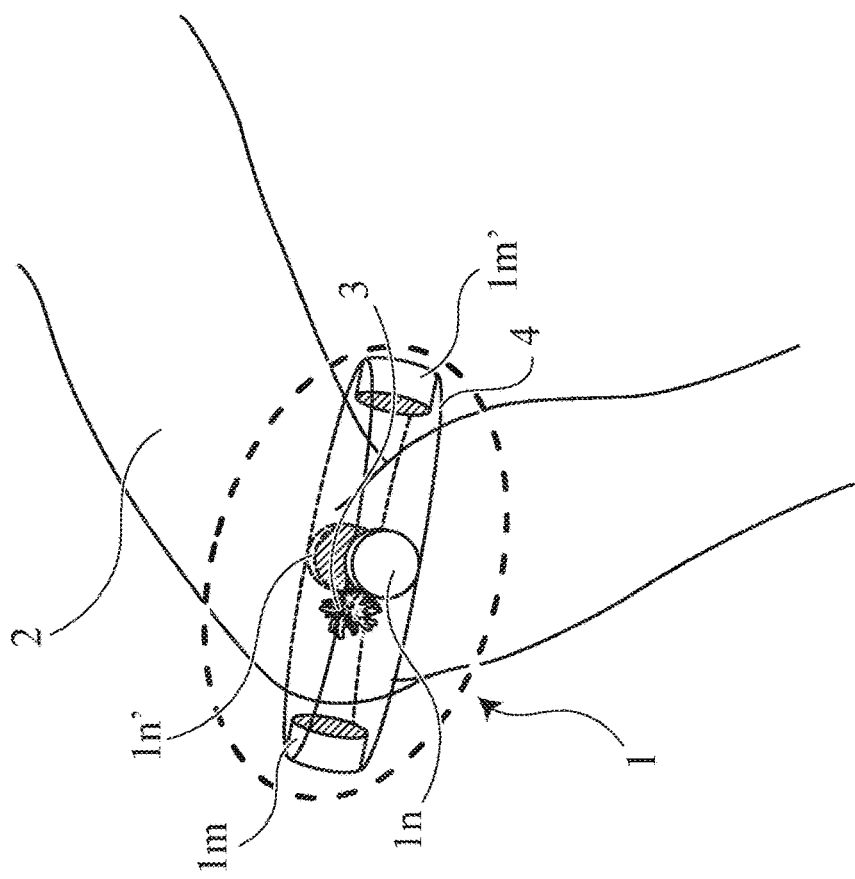
FIG. 4A shows an example of the placement of an arrangement of electromagnetic transducers in contact and targeting a tissue in the knee area of an individual.

FIG. 4A illustrates the disposition of an arrangement of electromagnetic transducers (1) over a volume (2) which consists of the knee of an individual. In the interior of the knee is a tissue (3) which it is desired to stimulate electromagnetically. Said arrangement of electromagnetic transducers (1) comprises two pairs of transducers as detailed below:

A first pair of transducers: a transducer (1m) and a transducer (1m') and a second pair of transducers: a transducer (1n) and a transducer (1n').

Said pairs of transducers are disposed around the knee in the position of the tissue (3) at the height of the patella and such that the active faces of the transducers face each other in the direction of the position of the tissue (3).

In addition, the arrangement (1) optionally meets a condition of orthogonality in that a plane parallel to any of the surfaces of the active faces of the first pair of transducers is orthogonal to another plane parallel to any of the surfaces of the active faces of the second, and third pair of transducers, and in addition, any plane parallel to the surfaces of the active faces of the second pair of transducers is orthogonal to any other plane parallel to any of the surfaces of the active faces of the first and third pair of transducers, and in addition, projections of the planes of the active faces pointed toward the tissue cover the maximum surface possible of said tissue, with this configuration ensuring optimum stimulation of the tissue.

It may also be possible that the transducers that comprise each pair of transducers are not completely aligned or parallel to each other, or do not preserve the condition of orthogonality of the transducers described in the previous paragraph, may also succeed in stimulating the tissue (3).

Figure 4B:
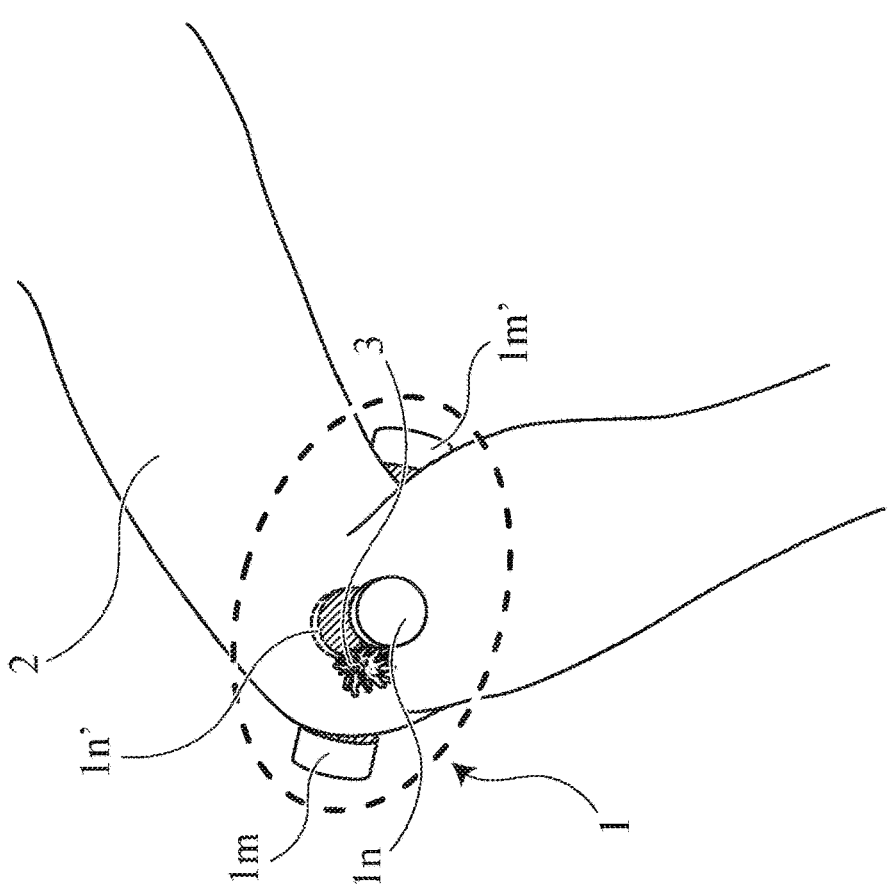
FIG. 4B shows an example of the placement of an arrangement of electromagnetic transducers without contact and targeting a tissue in the knee area of an individual.

FIG. 4B illustrates a similar disposition of the transducers, but where the active faces of the transducers are a distance of between 0.01 cm and 50 cm from the surface of the skin in the individual, supported on a frame (4), and optionally between 0.01 cm and 4 cm.

Going to stage (b) of the method of this disclosure, stage (b) consists of measuring the tissue impedance response stimulated in stage (a). When the frequency scanning is applied to the tissue, the tissue responds with a variation of its parameters which are measured, optionally, using the same electromagnetic transducers. This measurement of stimulated tissue acts as feedback and makes it possible to dynamically change the characteristics of the signal of stage (a).

Later, stage (c) of this method makes it possible to establish a reference level with the tissue impedance response measured in stage (b). Said reference level may be established by a user or determined as a maximum tissue impedance response during a determined time.

Continuing with stage (d) of this method, this stage consists of setting a tolerance (NT) at the reference level established in stage (c). This NT corresponds to a value in a percentage of the reference level established in stage (c), and can be defined in a computing unit, or be entered by a user.

In an example of the method, in an example, in stage (d), the NT can be between 5% and 60% and optionally between 25% and 50%.

Optionally, the NT can be selected between a range from 5% to 10%, from 10% to 15%, from 15% to 20%, from 20% to 25%, from 25% to 30%, from 30% to 35%, from 35% to 40%, from 40% to 45%, from 45% to 50%, from 50% to 55%, from 55% to 60%,from 5% to 10%, from 5% to 15%, from 5% to 20%, from 5% to 25%, from 5% to 30%, from 5% to 35%, from 5% to 40%, from 5% to 45%, from 5% to 50%, from 5% to 55%, from 5% to 60%,from 5% to 60%, from 60% to 55%, from 55% to 50%, from 50% to 45%, from 45% to 40%, from 40% to 35%, from 35% to 30%, from 30% to 25%, from 25% to 20%, from 20% to 15%, from 15% to 10%, from 10% to 5%.

The following stage e) of the method consists of determining lower tissue stimulation frequencies ($f_{bx}$) as the point where the tissue impedance response falls below the tolerance (NT) established in stage (d). For example, three $f_{bx}$, are determined, a first $f_{b1}$ equal to 75 kHz, a second $f_{b2}$ equal to 300 kHz, a third $f_{b3}$ equal to 450 kHz.

Next, stage f) of the method makes it possible to determine higher tissue stimulation frequencies ($f_{tx}$) as the point where the tissue impedance response returns to the tolerance (NT) established in stage (d). For example, three $f_{tx}$, are determined, a first $f_{t1}$ equal to 100 kHz, a second $f_{t2}$ equal to 350 kHz, a third $f_{t3}$ equal to 495 kHz.

Alternatively, in one example, the $f_{tx}$ are greater than the $f_{bx}$.

In another example of the method, in stage (e), the range of frequencies between the lower tissue stimulation frequency ($f_{bx}$) and the upper tissue stimulation frequency ($f_{tx}$) correspond to the central tissue frequencies.

The central tissue frequencies refer to the frequencies in which the electromagnetic stimulation is attenuated due to the effects of energy absorption in the tissue, for example, the electromagnetic stimulation signal falls below 25% of a tolerance level (NT).

In addition to the above said, the following of this disclosure allows determining stimulation frequency bands in order to focus stimuli in said bands until the tissue impedance response returns to an tolerance level or exceeds a maximum stimulation time.

Figure 12:
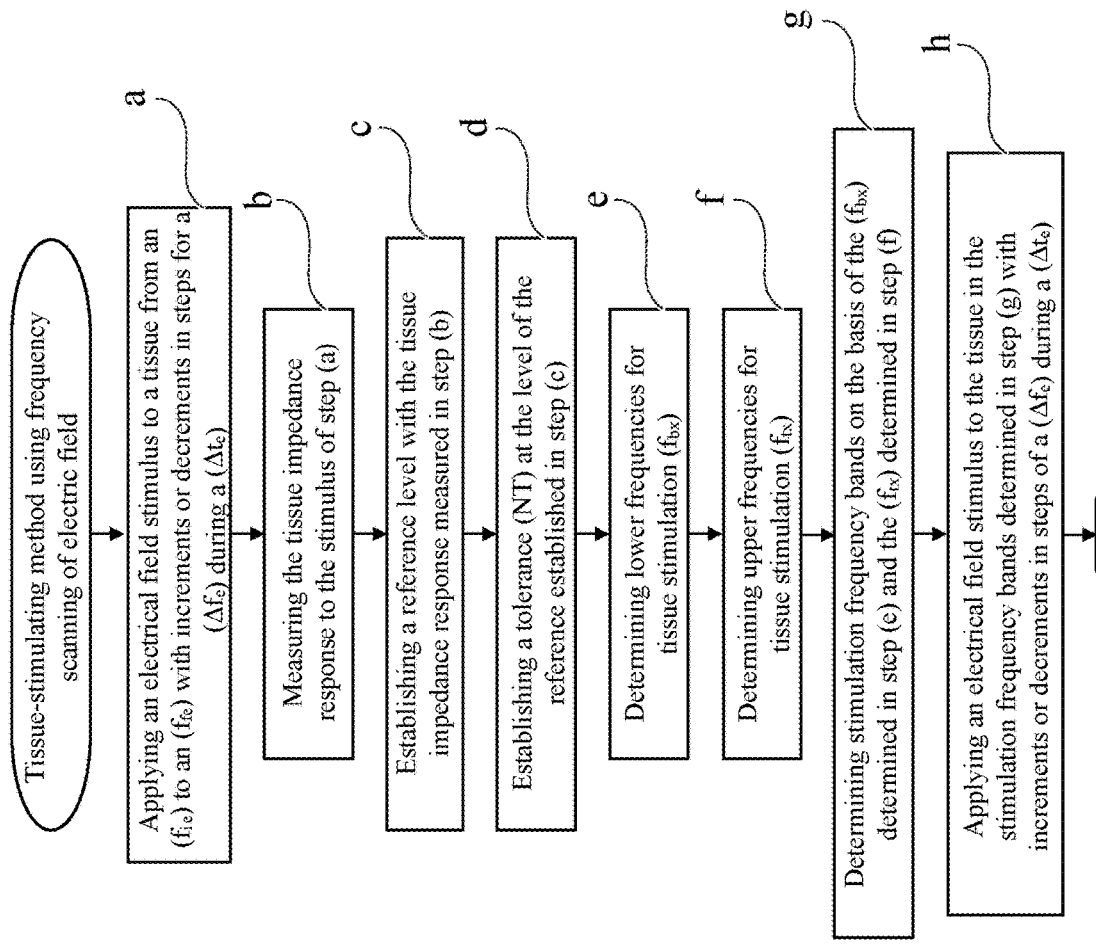
FIG. 12 shows a flow diagram of the method for tissue stimulation with frequency scan electric fields.

In reference to FIG. 12, the first method of tissue stimulation with frequency scan electrical field comprises the following additional stages:

in a stage (g) stimulation frequency bands based on the lower tissue stimulation frequencies ($f_{bx}$) determined in stage (e) along with the higher tissue stimulation frequencies ($f_{tx}$) determined in stage (f) are determined; and in a stage h) applying an electric field stimulus to a tissue through an arrangement of electromagnetic transducers that receive an activation signal, the frequency of which varies by the frequency stimulation bands determined in stage (g) with increments or decrements in steps of a frequency delta ($\Delta f_e$) during a time delta ($\Delta t_e$). In this way, for example, it is possible to define the frequency ranges of interest in order to execute frequency scanning focused on said frequency bands and to make it possible to stimulate the tissue more rapidly than scanning the entire range of frequencies between $f_{ie}$ and $f_{fe}$.

In a specific example, two $f_{tx}$ are determined: a first $f_{t1}$ equal to 100 kHz and a second $f_{t2}$ equal to 350 kHz in stage (e) and two $f_{bx}$ are determined: a first $f_{b1}$ equal to 75 kHz and a second $f_{b2}$ equal to 300 kHz in stage (f). A first frequency stimulation band corresponds to the frequencies between $f_{b1}$ and $f_{t1}$ and a second frequency stimulation band corresponds to the frequencies between $f_{b2}$ and $f_{t2}$.

A number "x" of frequency stimulation bands can be determined, with "x" being a natural number greater than or equal to 1, that is, from a band between $f_{b1}$ and $f_{t1}$, continuing with a second band between $f_{b2}$ and $f_{t2}$ to a band between $f_{bx}$ and $f_{tx}$.

In one example of the method, a stimulus is applied in a first band of stimulation frequencies from a frequency of $f_{b1}$ equal to 75 kHz and $f_{t1}$ equal to 100 kHz in steps from $\Delta f_e$ of 100 Hz in time deltas of $\Delta t_e$ equal to 10 minutes and a second stimulus in a second band of stimulation frequencies from a frequency $f_{b2}$ equal to 300 kHz and $f_{t2}$ equal to 350 kHz in steps of $\Delta f_e$ of 1 kHz in time deltas $\Delta t_e$ equal to 5 minutes.

The $f_{ie}$ and $f_{fe}$, the $\Delta f_e$, the NT and the $\Delta t_e$ can all be set by a user in a computing unit and stored in a memory record.

The $\Delta f_e$ may be a value between 0.1 Hz and 1 kHz, the $\Delta t_e$ may be between about 1 second and about 1 hour, and optionally between about 1 minute and about 1 hour.

As used herein "about" refers to +20% to −20% variation.

Optionally, the $\Delta f_e$ can be selected from about 0.1 Hz to about 1 Hz, from about 0.3 Hz to about 0.8 Hz, from about 0.5 Hz to about 0.6 Hz, from about 0.7 Hz to about 0.4 Hz, from about 0.9 Hz to about 0.2 Hz, from about 0.3 Hz to about 1 Hz, from about 0.5 Hz to about 1 Hz, from about 0.7 Hz to about 1 Hz, from about 0.9 Hz to about 1 Hz, from about 0.1 Hz to about 0.8 Hz, from about 0.1 Hz to about 0.6 Hz, from about 0.1 Hz to about 0.4 Hz, from about 0.1 Hz to about 0.2 Hz, from about 0.3 Hz to about 0.5 Hz, from about 0.5 Hz to about 0.7 Hz, from about 0.7 Hz to about 0.9 Hz, from about 0.1 Hz to about 1000 Hz, from about 100 Hz to about 900 Hz, from about 200 Hz to about 800 Hz, from about 300 Hz to about 700 Hz, from about 400 Hz to about 600 Hz, from about 500 Hz to about 500 Hz, from about 600 Hz to about 400 Hz, from about 700 Hz to about 300 Hz, from about 800 Hz to about 200 Hz, from about 900 Hz to about 100 Hz, from about 1000 Hz to about 0.1 Hz, from about 100 Hz to about 1000 Hz, from about 200 Hz to about 1000 Hz, from about 300 Hz to about 1000 Hz, from about 400 Hz to about 1000 Hz, from about 500 Hz to about 1000 Hz, from about 600 Hz to about 1000 Hz, from about 700 Hz to about 1000 Hz, from about 800 Hz to about 1000 Hz, from about 900 Hz to about 1000 Hz, from about 0.1 Hz to about 900 Hz, from about 0.1 Hz to about 800 Hz, from about 0.1 Hz to about 700 Hz, from about 0.1 Hz to about 600 Hz, from about 0.1 Hz to about 500 Hz, from about 0.1 Hz to about 400 Hz, from about 0.1 Hz to about 300 Hz, from about 0.1 Hz to about 200 Hz, from about 0.1 Hz to about 100 Hz, from about 100 Hz to about 200 Hz, from about 200 Hz to about 300 Hz, from about 300 Hz to about 400 Hz, from about 400 Hz to about 500 Hz, from about 500 Hz to about 600 Hz, from about 600 Hz to about 700 Hz, from about 700 Hz to about 800 Hz, from about 800 Hz to about 900 Hz, from about 900 Hz to about 1000 Hz.

In addition, an example of the method is possible, in an example, where the $f_{tx}$ are less than the $f_{bx}$ and in stage (a) decrements are made in steps with a frequency delta of $\Delta f_e$, during a $\Delta t_e$ in the frequency of the activation signal.

Returning to stage (a) of the method, the activation signal with the frequency that varies from an initial tissue stimulation frequency ($f_{ie}$) to a final tissue stimulation frequency ($f_{fe}$) can be applied to a transducer by means of an arrangement of multiplexers that make it possible that one or more electrical field stimulation signals are applied to each transducer at a determined time, sequentially, out of phase in relation to the other stimulation signal or to various stimulation signals, randomly or according to a program established for each of the transducers.

Figure 7:
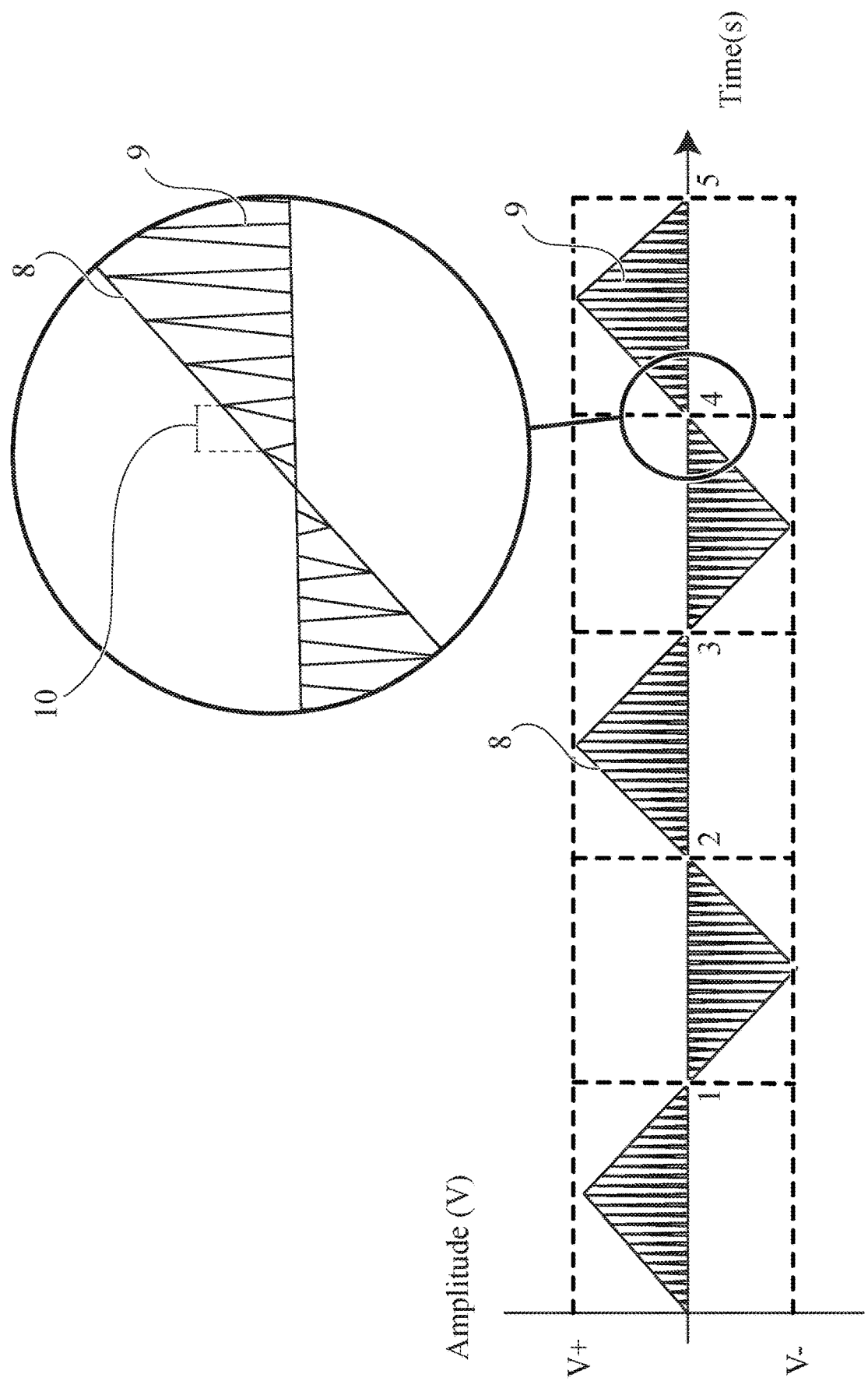
FIG. 7 shows an example of an activation signal in alternating triangular-wave shape.
Figure 8:
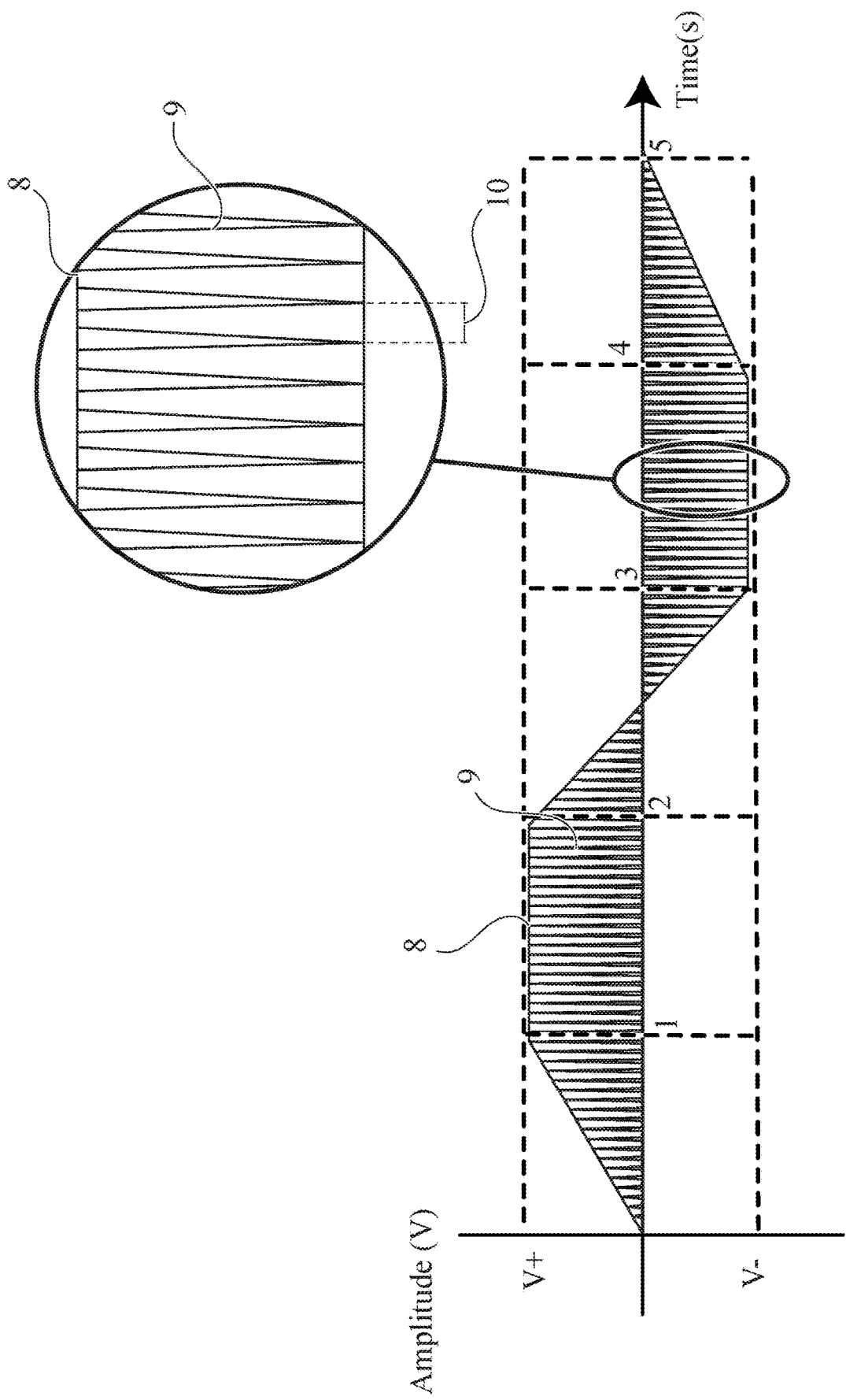
FIG. 8 shows an example of a segmented activation signal which combines alternating ramp signals with alternating square-wave signals.

In reference to FIGS. 7 and 8, it will be understood that an activation signal may be comprised of a modulating signal (8) and a carrier signal (9), the carrier signal (9) is optionally of a frequency order greater than that of the modulating signal (8).

In an example of the method, the modulating signal (8) has a frequency of 100 kHz, while the carrier signal (9) has a frequency of less than 1 kHz.

In an example of the method, the $f_{ie}$ and the $f_{fe}$ are between 0.1 Hz and 1000 kHz for both the carrier signal (9) and the modulating signal (8).

Optionally, the frequency of $f_{ie}$ and the $f_{fe}$ may be selected from the following ranges: from about 0.1 Hz to about 1 Hz, from about 0.3 Hz to about 0.8 Hz, from about 0.5 Hz to about 0.6 Hz, from about 0.7 Hz to about 0.4 Hz, from about 0.9 Hz to about 0.2 Hz, from about 0.3 Hz to about 1 Hz, from about 0.5 Hz to about 1 Hz, from about 0.7 Hz to about 1 Hz, from about 0.9 Hz to about 1 Hz, from about 0.1 Hz to about 0.8 Hz, from about 0.1 Hz to about 0.6 Hz, from about 0.1 Hz to about 0.4 Hz, from about 0.1 Hz to about 0.2 Hz, from about 0.3 Hz to about 0.5 Hz, from about 0.5 Hz to about 0.7 Hz, from about 0.7 Hz to about 0.9 Hz, from about 0.1 Hz to about 1000 Hz, from about 100 Hz to about 900 Hz, from about 200 Hz to about 800 Hz, from about 300 Hz to about 700 Hz, from about 400 Hz to about 600 Hz, from about 500 Hz to about 500 Hz, from about 600 Hz to about 400 Hz, from about 700 Hz to about 300 Hz, from about 800 Hz to about 200 Hz, from about 900 Hz to about 100 Hz, from about 1000 Hz to about 0.1 Hz, from about 100 Hz to about 1000 Hz, from about 200 Hz to about 1000 Hz, from about 300 Hz to about 1000 Hz, from about 400 Hz to about 1000 Hz, from about 500 Hz to about 1000 Hz, from about 600 Hz to about 1000 Hz, from about 700 Hz to about 1000 Hz, from about 800 Hz to about 1000 Hz, from about 900 Hz to about 1000 Hz, from about 0.1 Hz to about 900 Hz, from about 0.1 Hz to about 800 Hz, from about 0.1 Hz to about 700 Hz, from about 0.1 Hz to about 600 Hz, from about 0.1 Hz to about 500 Hz, from about 0.1 Hz to about 400 Hz, from about 0.1 Hz to about 300 Hz, from about 0.1 Hz to about 200 Hz, from about 0.1 Hz to about 100 Hz, from about 100 Hz to about 200 Hz, from about 200 Hz to about 300 Hz, from about 300 Hz to about 400 Hz, from about 400 Hz to about 500 Hz, from about 500 Hz to about 600 Hz, from about 600 Hz to about 700 Hz, from about 700 Hz to about 800 Hz, from about 800 Hz to about 900 Hz, from about 900 Hz to about 1000 Hz, from about 100 kHz to about 900 kHz, from about 200 kHz to about 800 kHz, from about 300 kHz to about 700 kHz, from about 400 kHz to about 600 kHz, from about 100 kHz to about 1000 kHz, from about 200 kHz to about 1000 kHz, from about 300 kHz to about 1000 kHz, from about 400 kHz to about 1000 kHz, from about 500 kHz to about 1000 kHz, from about 600 kHz to about 1000 kHz, from about 700 kHz to about 1000 kHz, from about 800 kHz to about 1000 kHz, from about 900 kHz to about 1000 kHz, from about 0.0001 kHz to about 900 kHz, from about 0.0001 kHz to about 800 kHz, from about 0.0001 kHz to about 700 kHz, from about 0.0001 kHz to about 600 kHz, from about 0.0001 kHz to about 500 kHz, from about 0.0001 kHz to about 400 kHz, from about 0.0001 kHz to about 300 kHz, from about 0.0001 kHz to about 200 kHz, from about 0.0001 kHz to about 100 kHz, from about 100 kHz to about 200 kHz, from about 200 kHz to about 300 kHz, from about 300 kHz to about 400 kHz, from about 400 kHz to about 500 kHz, from about 500 kHz to about 600 kHz, from about 600 kHz to about 700 kHz, from about 700 kHz to about 800 kHz, from about 800 kHz to about 900 kHz, from about 900 kHz to about 1000 kHz, from about 1 Hz to about 500 kHz, from about 1 kHz to about 500 kHz, from about 1 kHz to about 50 kHz, from about 1 Hz to about 50 kHz.

In reference to FIG. 5A, a frequency vs. time graph is observed, which corresponds to a modulating signal (8) for an activation signal for tissue stimulation with frequency scan electromagnetic fields. In this example, said modulating signal (8) increases its frequency every second by applying a Δf of 1 Hz, from an initial frequency of 1 Hz to a final frequency of 5 Hz, each frequency being applied for a Δt of 1 s.

In reference to FIG. 5B, an example is shown of the activation signal by an electromagnetic stimulation applied to the electromagnetic transducers in which the modulating signal (8) has a sinusoidal form and its frequency varies from an initial frequency of 1 Hz to 5 Hz with Δf of 1 Hz each second, from 1 to 5 s. The carrier signal (9) is an impulse type signal with a fixed period (10) of 2 ms or a fixed frequency of 500 Hz.

In reference to FIG. 5C, an example is shown of the activation signal for an electromagnetic stimulation in which the modulating signal (8) has a squared form and its frequency varies from an initial frequency of 1 Hz to 5 Hz with Δf of 1 Hz each second, from 1 to 5 s. The carrier signal (9) is a pulsing type signal with a fixed period (10) of 100 ms or a fixed frequency of 10 kHz.

Figure 6:
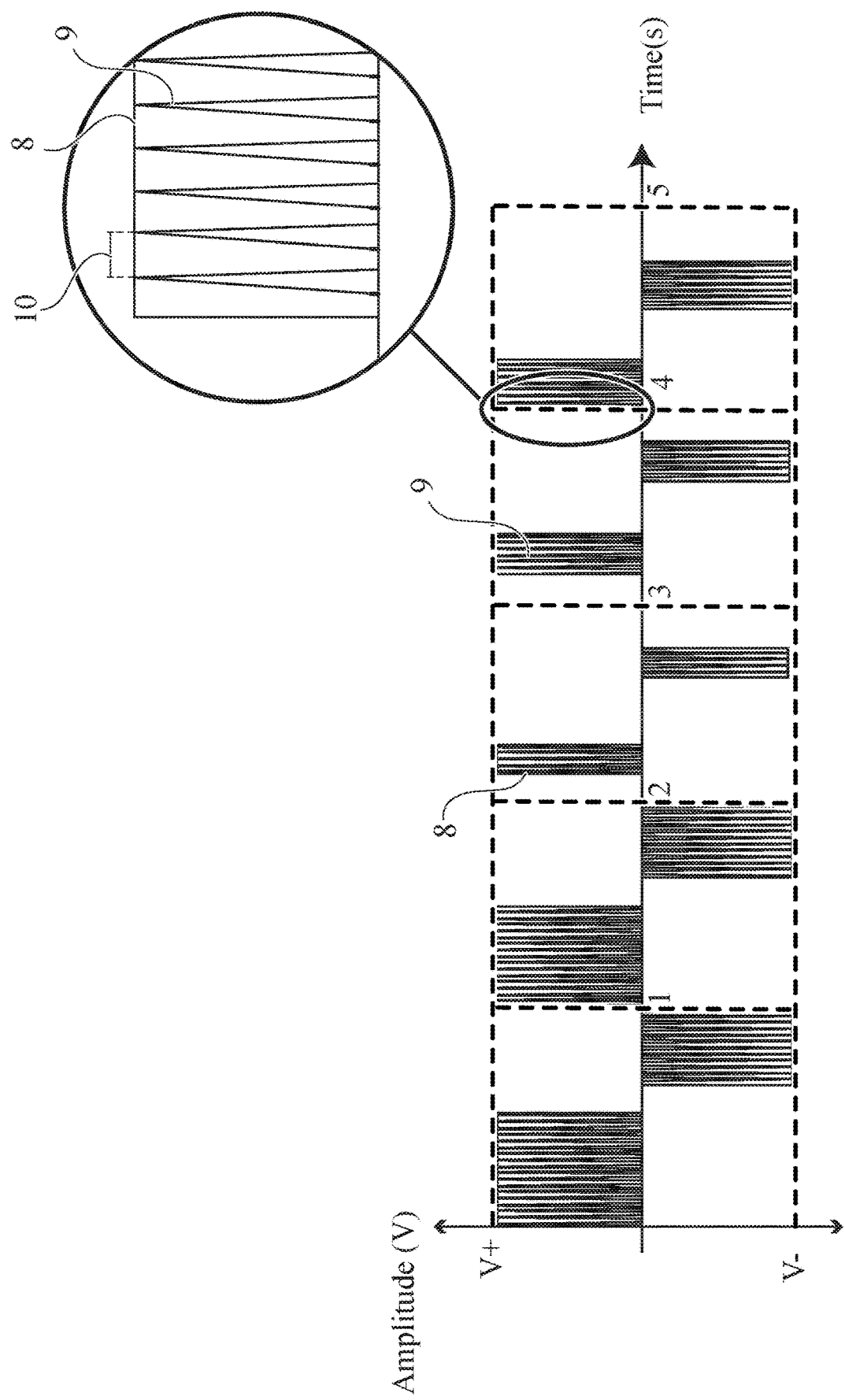
FIG. 6 shows an example of an alternating square-wave activation signal with variation of the duty cycle.

In reference to FIG. 6, an example is shown of the activation signal for an electromagnetic stimulation in which the modulating signal (8) has an alternating square wave shape and variation of the duty cycle, its frequency remains fixed, and the carrier signal (9) is of the pulsing type with a fixed period (10) of 200 µs or a fixed frequency of 5 kHz.

In reference to FIG. 7, an example is shown of the activation signal for an electromagnetic stimulation with which the modulating signal (8) has the alternating triangular wave shape, its frequency is fixed, and the carrier signal (9) is of the pulsing type with a fixed period (10) of 2 µs or a fixed frequency of 500 kHz.

In reference to FIG. 8, an example is shown of the activation signal for electromagnetic stimulation in which the modulating signal (8) has a segmented type function that combines an alternating ramp and alternating square wave shape signal, the carrier signal (9) is of the pulsing type with a fixed period (10) of 2 µs or a fixed frequency of 500 kHz.

In an example of this disclosure, the modulating signal (8) changes the duty cycle dynamically based on the response of the tissue impedance response measured in the stage (b). Said duty cycle is between 0% and 100% and makes it possible to change the electrical power applied per transducer or transducers to the tissue (3). A duty cycle of 0% can be used, for example, to halt the activation of the signal for a determined period of time.

Optionally the duty cycle of the modulating signal (8) and/or the carrier signal (9) of the activation signal can be selected from 0% to 100%, from 5% to 95%, from 10% to 90%, from 15% to 85%, from 20% to 80%, from 25% to 75%, from 30% to 70%, from 35% to 65%, from 40% to 60%, from 45% to 55%, from 10% to 100%, from 20% to 100%, from 30% to 100%, from 40% to 100%, from 50% to 100%, from 60% to 100%, from 70% to 100%, from 80% to 100%, from 90% to 100%, from 0% to 90%, from 0% to 80%, from 0% to 70%, from 0% to 60%, from 0% to 50%, from 0% to 40%, from 0% to 30%, from 0% to 20%, from 0% to 10%, from 10% to 20%, from 20% to 30%, from 30% to 40%, from 40% to 50%, from 50% to 60%, from 60% to 70%, from 70% to 80%, from 80% to 90%, from 90% to 100%.

In reference to FIG. 9A, an example of the tissue impedance response is shown, where a tissue is stimulated with frequency scan electromagnetic fields from an initial frequency stimulation ($f_i$) to a final stimulation frequency ($f_f$).

Initiating from $f_i$, the tissue impedance response is measured and graphed, said response begins with a response value for the tissue impedance that oscillates around a maximum amplitude value (A1) as the tissue stimulation frequency increases in steps from $\Delta f$ each determined $\Delta t$.

Continuing with the increments of the stimulation frequency value, the tissue impedance response value falls below the tolerance level value (NT) of the tissue impedance response. This frequency value is designated as the lower tissue stimulation frequency ($f_{bx}$).

As the tissue stimulation frequency increases, the tissue impedance response continues to fall to a minimum amplitude value (A0), and said minimum value is maintained in alignment with tissue stimulation frequency increases.

As the frequency value increases, the tissue impedance response value begins to rise until it reaches a tissue impedance response value that oscillates around (A1). This frequency value is designated as the upper tissue stimulation frequency ($f_{tx}$) which is maintained until $f_f$ is reached.

In citing of $f_i$, $f_r$, $\Delta f$, and $\Delta t$ without the subscript "e" ($f_{ie}$, $f_{fe}$, $\Delta f_e$, and $\Delta t_e$) or "m" ($f_{im}$, $f_{fm}$, $\Delta f_m$ and $\Delta t_m$), these will be understood to refer to either of the two phenomena, namely, magnetic field or electric field.

In reference to FIG. 9B, corresponds to the approximate representation of the response of the example described in FIG. 9A, in which the tissue impedance response is smoothed through the use of averages of the tissue impedance response impedance values, for example, by using digital filters to produce said smoothening.

The digital filters are selected from, among others, of the group of filters that consist of FIR, Parks-McClellan, minimum squares, Kaiser windows, IIR filters, such as Butterworth, Chebyshev, elliptical filters, among others known to a person versed in the art. It is understood that the purpose of smoothening the signal is to eliminate signal noise or to eliminate atypical values, through a simple average or through digital filters.

In reference to FIG. 9C, an example is shown of the tissue impedance response, where a tissue is stimulated with electromagnetic fields with frequency scan from an initial frequency stimulation ($f_i$) to a final stimulation frequency ($f_f$).

Initiating from $f_{ie}$, the tissue impedance response is measured and graphed, said response begins with a response value for the tissue impedance that oscillates around a maximum amplitude value (A1) as the tissue stimulation frequency increases in steps from $\Delta f$ at each determined $\Delta t$.

Continuing with the increments of the stimulation frequency value, the tissue impedance response value falls below the tolerance level value (NT) of the tissue impedance response. This frequency value is designated as the lower tissue stimulation frequency ($f_{bx}$).

As the tissue stimulation frequency increases, the tissue impedance response continues to fall to a minimum amplitude value (A0), and said minimum value is maintained in alignment with tissue stimulation frequency increases until it reaches a final stimulation frequency ($f_f$).

In reference to FIG. 9D, corresponds to an example of the approximate representation of the response of the example described in FIG. 9C, in which the tissue impedance response is smoothed through the use of averages of the tissue impedance response impedance values, for example, by using digital filters to produce said smoothening.

Figure 13:
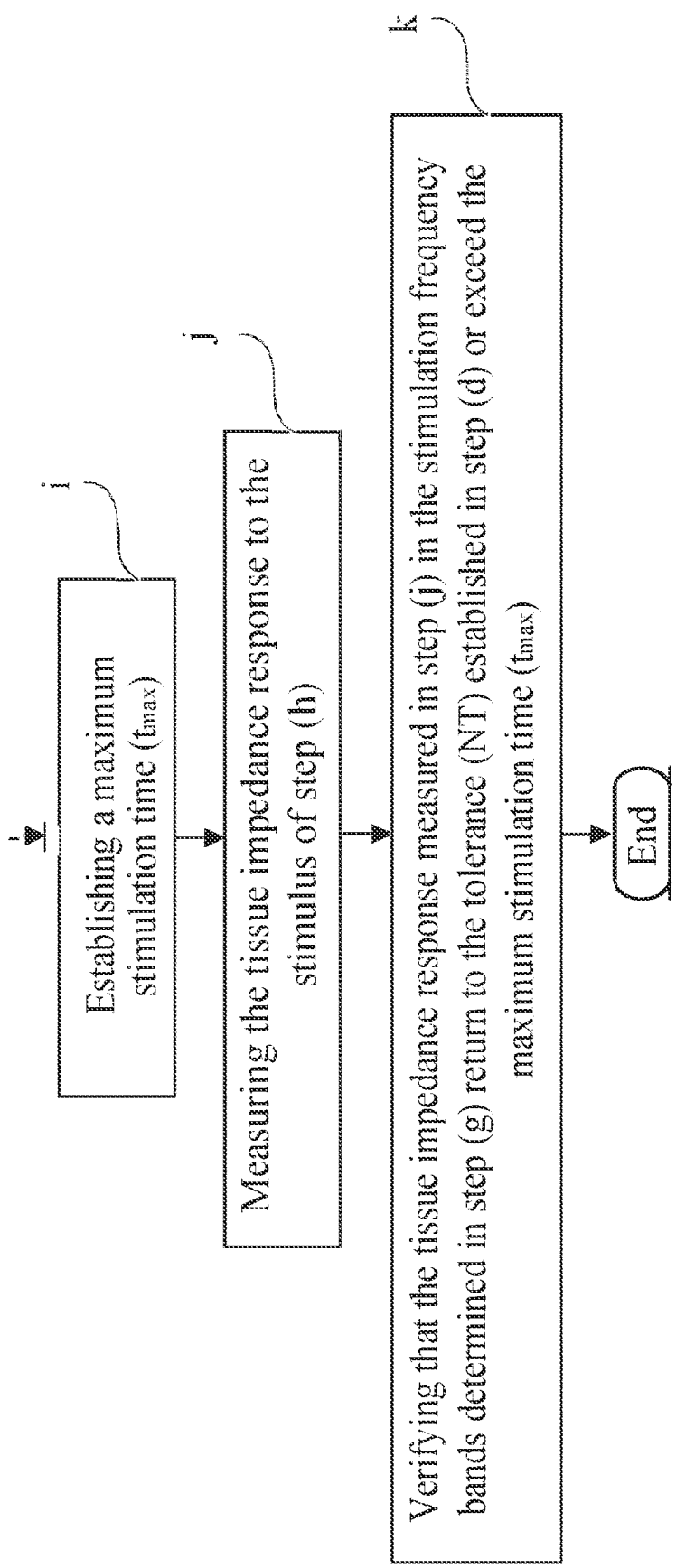
FIG. 13 shows a flow diagram of the method for tissue stimulation with frequency scan electric fields with additional stages.

In another example of this method, and in reference to FIG. 13, after stage (h) of the method already described above, the following additional stages are followed:

i) establishing a maximum stimulation time ($t_{max}$), which allows to protect the tissue from being overstimulated;

j) measuring the tissue impedance response to the stimulus of stage (h);

k) verifying that the tissue impedance response measured in stage (j) in the stimulation frequency bands determined in stage (g) return to the tolerance (NT) established in stage (d) or exceed the maximum stimulation time ($t_{max}$).

In an example of this method, $t_{max}$, of stage (i) may be between about 1 hour and about 18 hours. When referring to the $t_{max}$ "about" should be understood as a 5% variation of the maximum stimulation time.

Figure 14:
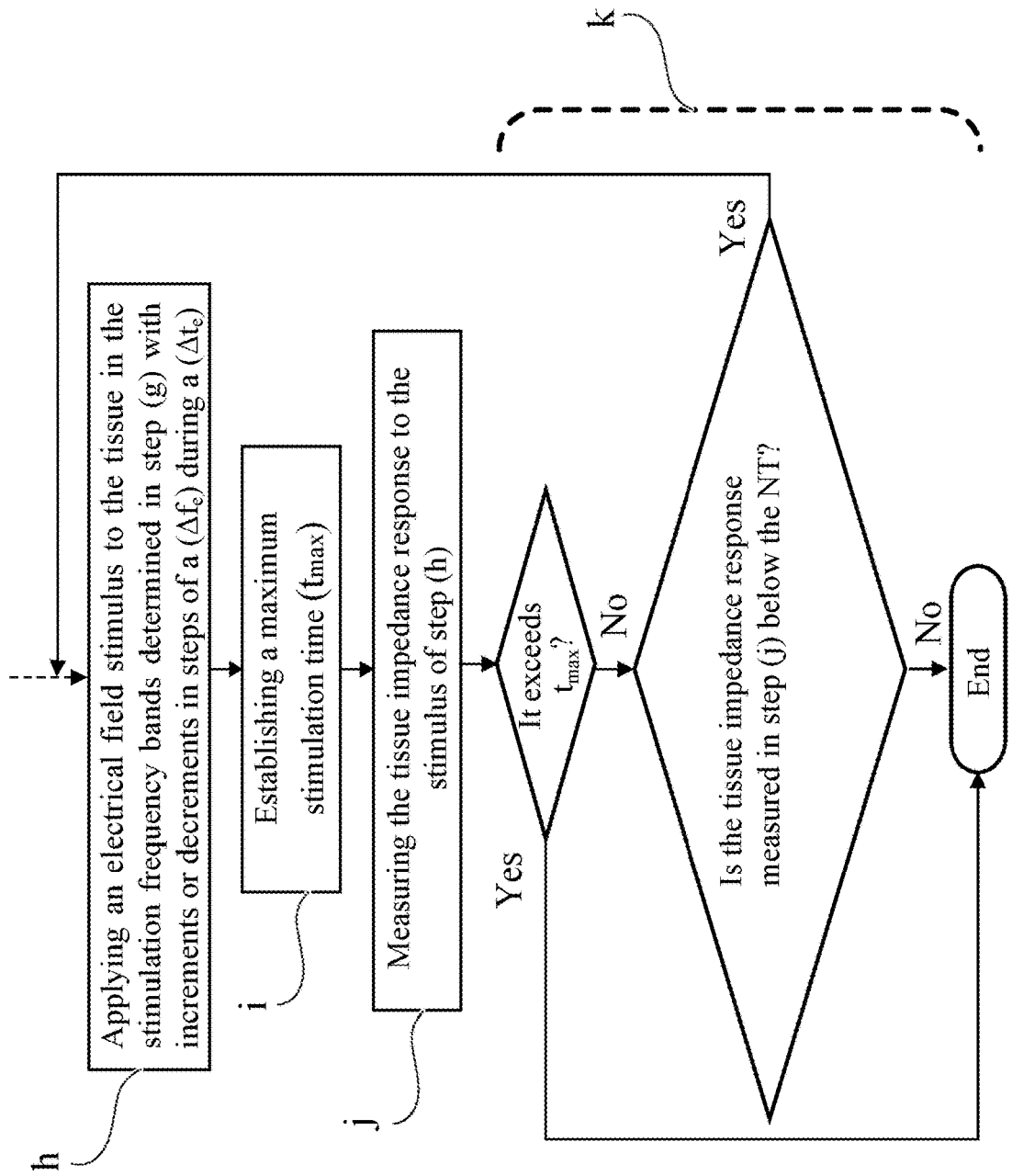
FIG. 14 shows a flow diagram of the method for tissue stimulation with frequency scan electric fields in which stage k is disaggregated.

In specific example of this method, and in reference to FIG. 14, in stage (k), the following verifications are conducted:

if the maximum stimulation time ($t_{max}$) is exceeded, then finalizing;

if the maximum stimulation time ($t_{max}$) is not exceeded, and the tissue impedance response measured in stage (j) is below the tolerance (NT) established in stage (d), repeating stage (h);

if the tissue impedance response measured in stage (j) in the stimulation frequency bands determined in stage (g) exceed the tolerance (NT) established in stage (d), then finalizing;

In reference to FIG. 10A, an example is shown of the tissue impedance response of a tissue stimulated with electrical field or magnetic field by frequency scan from a $f_i$. The tissue impedance response is measured and graphed simultaneously. Said response begins with a tissue impedance response value that oscillates around a maximum amplitude value (A1).

As the tissue stimulation frequency increases in steps from $\Delta f$, it continues oscillating around (A1) until the stimulation frequency reaches a first lower tissue stimulation frequency ($f_{b1}$), which corresponds to a point at which the tissue impedance response value falls below the NT.

As the tissue stimulation frequency continues to increase, the tissue impedance response value continues to fall to a tissue impedance response value that oscillates around a minimum amplitude value (A0) where it is maintained until the tissue impedance response value begins to increase until it reaches the (A1). This point is a first upper tissue stimulation frequency ($f_{t1}$).

The range of frequencies between $f_{b1}$ and $f_{t1}$ is a first stimulation band.

Continuing the tissue stimulation frequency increase, a second stimulation frequency band range is found in a range of frequencies between $f_{b2}$ and $f_{t2}$, a third stimulation frequency band range is found in a range of frequencies between $f_{b3}$ and $f_{t3}$, and a fourth stimulation frequency band range is found in a range of frequencies between $f_{b4}$ and $f_{t4}$, until frequency stimulation reaches $f_f$.

These stimulation bands refer to a range of central tissue frequencies which present a biochemical imbalance.

Optionally, another example of the method for stimulating a tissue with electromagnetic fields, at stage (e), the range of frequencies between the lower tissue stimulation frequency ($f_{bx}$) and the upper tissue stimulation frequency ($f_{tx}$) correspond to the central tissue frequencies.

Alternatively, another example of the method for stimulating a tissue with electromagnetic fields, the activation signal for the electrical field transducers changes with tissue temperature feedback.

In another example of the method for stimulating a tissue with electromagnetic fields, the stimulated biological tissue is in an animal.

Another example of the method for stimulating a tissue with electromagnetic fields, the stimulated biological tissue is an animal.

Alternatively, another example of the method for stimulating a tissue with electromagnetic fields, the electromagnetic transducers are in contact with an external surface of the tissue.

In yet another example of the method for stimulating a tissue with electromagnetic fields the electromagnetic transducers are located a determined distance from an external surface of the biological tissue.

In an example of the method for stimulating a tissue with electromagnetic fields, a first portion of the electromagnetic transducers are in contact with an external surface of the biological tissue and a second portion of the electromagnetic transducers are located a determined distance from the external surface of the biological tissue.

Optionally, another example of the method for stimulating a tissue with electromagnetic fields, the electromagnetic transducers are activated according to a defined sequence.

Alternatively, another example of the method for stimulating a tissue with electromagnetic fields, the electromagnetic transducers are activated randomly.

Optionally, another example of the method for stimulating a tissue with electromagnetic fields, the activation signal is applied to each transducer at a determined time, sequentially, out of phase in relation to the other activation signal or to various stimulation signals, randomly or according to a program established for each one of the transducers.

In reference to FIG. 10B, corresponds to the approximate representation of the response of the example described in FIG. 10A, in which the tissue impedance response is smoothed, for example, through the use of averages of the response values in amplitude, using the tools described above.

In addition, in one example of the method, in stage (a), a magnetic field stimulus is applied through the arrangement of electromagnetic transducers that receive an activation signal, the frequency of which varies from an initial tissue stimulation frequency ($f_{im}$) to a final tissue stimulation frequency ($f_{fm}$), with increases or decreases in steps of a frequency delta ($\Delta f_m$) during a time delta ($\Delta t_m$), which makes it possible to obtain benefits from a combined stimulation with magnetic field and electrical field, such as, for example, broadening the electrical field stimulation area of the tissue. In another example, in stage (a), the magnetic field stimulus is orthogonal to the electrical field stimulus.

The magnetic field transducers are optionally arranged such that they generate magnetic fields orthogonal to the electrical fields of the electrical field transducers, such that, optimum stimulation of the tissue is provided.

Nonetheless, it may be possible for the magnetic field transducers to be arranged in different configurations, in which the magnetic fields generated by said magnetic field transducers are not orthogonal to the electrical fields generated by electrical field transducers in the arrangement.

In another example of this disclosure, for example, the transducers of the arrangement of electromagnetic transducers (1) are magnetic field transducers and may or may not be faced by another magnetic field transducer or another electrical field transducer.

In order to activate the magnetic field transducers, the activation signal can be selected, among other things, from direct current or alternating current signal, pulsed signal, a train of alternating or non-alternating impulsive signals, square wave signal with variation of the duty cycle, triangular wave signal, sawtooth wave signal, modulated by amplitude (AM), modulated by frequency (PM), modulated by phase (PM), modulated by pulse positions (PPM), modulated by pulse width (PWM), and combinations of these.

Figure 15:
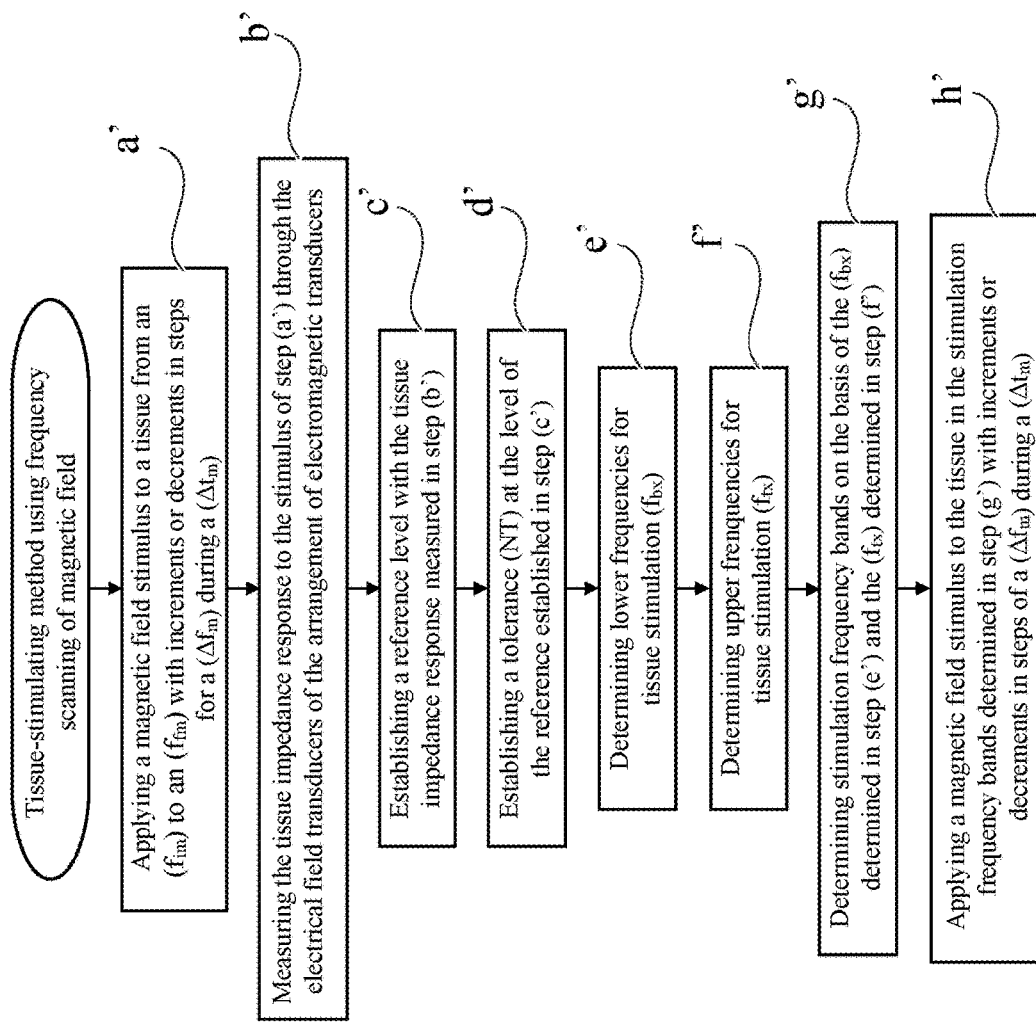
FIG. 15 shows a flow diagram of the method for tissue stimulation with frequency scan magnetic fields.

In reference to FIGS. 1 and FIG. 15, another method of the present disclosure is tissue stimulation using magnetic fields and comprising the following stages:

a') applying a magnetic field stimulus to a tissue through an arrangement of electromagnetic transducers that receive an activation signal the frequency of which varies from an initial tissue stimulation frequency ($f_{im}$) to a final tissue stimulation frequency ($f_{fm}$) with increments or decrements in steps of a frequency delta ($\Delta f_m$) during a time delta ($\Delta t_m$);

b') measuring the tissue impedance response to the magnetic field stimulus through the electrical field transducers of the arrangement of electromagnetic transducers;

c') establishing a reference level with the tissue impedance response measured in stage (b');

d') establishing a tolerance (NT) to the reference level established in stage (c');

e') determining lower tissue stimulation frequencies ($f_{bx}$) as the point where the tissue impedance response falls below the tolerance (NT) established in stage (d');

f') determining upper tissue stimulation frequencies ($f_{tx}$) as the point where the tissue impedance response returns to the tolerance (NT) established in stage (d');

wherein the upper tissue stimulation frequencies ($f_{tx}$) are greater than the lower tissue stimulation frequencies ($f_{bx}$) and "x" is a natural number greater than or equal to 1.

The magnetic transducers are arranged over a volume (2) that contains the tissue (3) to be stimulated. Each magnetic transducer generates a magnetic field that is applied to the tissue (3). The field generated with each transducer is controlled by an activation signal which, optionally, has an initial frequency ($f_{im}$) that changes over time to a final frequency ($f_{fm}$), which can be higher than, lower than or equal to the initial frequency.

In one example, the intensity of the magnetic field generated by the magnetic field transducers when activated by the activation signal, can be between 0.1 mT (milliteslas) equivalent to 1 Gauss, and 200 mT (milliteslas), equivalent to 2000 Gauss, and optionally between 40 mT (milliteslas) equivalent to 400 Gauss, and 200 mT (milliteslas), equivalent to 2000 Gauss.

Optionally, the intensity generated by the magnetic field transducers is selected among the range from 1 mT to 10 mT, from 10 mT to 20 mT, from 20 mT to 30 mT, from 30 mT to 40 mT, from 40 mT to 50 mT, from 50 mT to 60 mT, from 60 mT to 70 mT, from 70 mT to 80 mT, from 80 mT to 90 mT, from 90 mT to 100 mT, from 100 mT to 110 mT, from 110 mT to 120 mT, from 120 mT to 130 mT, from 130 mT to 140 mT, from 140 mT to 150 mT, from 150 mT to 160 mT, from 160 mT to 170 mT, from 170 mT to 180 mT, from 180 mT to 190 mT, from 190 mT to 200 mT,from 1 mT to 10 mT, from 1 mT to 20 mT, from 1 mT to 30 mT, from 1 mT to 40 mT, from 1 mT to 50 mT, from 1 mT to 60 mT, from 1 mT to 70 mT, from 1 mT to 80 mT, from 1 mT to 90 mT, from 1 mT to 100 mT, from 1 mT to 110 mT, from 1 mT to 120 mT, from 1 mT to 130 mT, from 1 mT to 140 mT, from 1 mT to 150 mT, from 1 mT to 160 mT, from 1 mT to 170 mT, from 1 mT to 180 mT, from 1 mT to 190 mT, from 1 mT to 200 mT, from 1 mT to 200 mT, from 200 mT to 190 mT, from 190 mT to 180 mT, from 180 mT to 170 mT, from 170 mT to 160 mT, from 160 mT to 150 mT, from 150 mT to 140 mT, from 140 mT to 130 mT, from 130 mT to 120 mT, from 120 mT to 110 mT, from 110 mT to 100 mT, from 100 mT to 90 mT, from 90 mT to 80 mT, from 80 mT to 70 mT, from 70 mT to 60 mT, from 60 mT to 50 mT, from 50 mT to 40 mT, from 40 mT to 30 mT, from 30 mT to 20 mT, from 20 mT to 10 mT.

The defined $\Delta t_m$ refers to a period of time which may vary as a function of the application required to use the method.

The $f_{im}$ and $f_{fm}$, the $\Delta f_m$ and the $\Delta t_m$ are set by a user in a computing unit and stored in a memory record. The applicable range values for $f_{im}$, $f_{fm}$, $\Delta f_m$ and $\Delta t_m$ for magnetic stimulation are the same used for $f_{ie}$, $f_{fe}$, $\Delta f_e$ and $\Delta t_e$ in electromagnetic stimulation cited previously in this disclosure.

Optionally the $f_{im}$ and $f_{fm}$ are in a range of frequencies between about 0.1 Hz and about 1000 kHz, and optionally between about 25 Hz and about 1000 kHz.

Alternatively, the frequency of $f_{im}$, and the $f_{fm}$ may be selected from the following ranges: from about 0.1 Hz to about 1 Hz, from about 0.3 Hz to about 0.8 Hz, from about 0.5 Hz to about 0.6 Hz, from about 0.7 Hz to about 0.4 Hz, from about 0.9 Hz to about 0.2 Hz, from about 0.3 Hz to about 1 Hz, from about 0.5 Hz to about 1 Hz, from about 0.7 Hz to about 1 Hz, from about 0.9 Hz to about 1 Hz, from about 0.1 Hz to about 0.8 Hz, from about 0.1 Hz to about 0.6 Hz, from about 0.1 Hz to about 0.4 Hz, from about 0.1 Hz to about 0.2 Hz, from about 0.3 Hz to about 0.5 Hz, from about 0.5 Hz to about 0.7 Hz, from about 0.7 Hz to about 0.9 Hz, from about 0.1 Hz to about 1000 Hz, from about 100 Hz to about 900 Hz, from about 200 Hz to about 800 Hz, from about 300 Hz to about 700 Hz, from about 400 Hz to about 600 Hz, from about 500 Hz to about 500 Hz, from about 600 Hz to about 400 Hz, from about 700 Hz to about 300 Hz, from about 800 Hz to about 200 Hz, from about 900 Hz to about 100 Hz, from about 1000 Hz to about 0.1 Hz, from about 100 Hz to about 1000 Hz, from about 200 Hz to about 1000 Hz, from about 300 Hz to about 1000 Hz, from about 400 Hz to about 1000 Hz, from about 500 Hz to about 1000 Hz, from about 600 Hz to about 1000 Hz, from about 700 Hz to about 1000 Hz, from about 800 Hz to about 1000 Hz, from about 900 Hz to about 1000 Hz, from about 0.1 Hz to about 900 Hz, from about 0.1 Hz to about 800 Hz, from about 0.1 Hz to about 700 Hz, from about 0.1 Hz to about 600 Hz, from about 0.1 Hz to about 500 Hz, from about 0.1 Hz to about 400 Hz, from about 0.1 Hz to about 300 Hz, from about 0.1 Hz to about 200 Hz, from about 0.1 Hz to about 100 Hz, from about 100 Hz to about 200 Hz, from about 200 Hz to about 300 Hz, from about 300 Hz to about 400 Hz, from about 400 Hz to about 500 Hz, from about 500 Hz to about 600 Hz, from about 600 Hz to about 700 Hz, from about 700 Hz to about 800 Hz, from about 800 Hz to about 900 Hz, from about 900 Hz to about 1000 Hz, from about 100 kHz to about 900 kHz, from about 200 kHz to about 800 kHz, from about 300 kHz to about 700 kHz, from about 400 kHz to about 600 kHz, from about 100 kHz to about 1000 kHz, from about 200 kHz to about 1000 kHz, from about 300 kHz to about 1000 kHz, from about 400 kHz to about 1000 kHz, from about 500 kHz to about 1000 kHz, from about 600 kHz to about 1000 kHz, from about 700 kHz to about 1000 kHz, from about 800 kHz to about 1000 kHz, from about 900 kHz to about 1000 kHz, from about 0.0001 kHz to about 900 kHz, from about 0.0001 kHz to about 800 kHz, from about 0.0001 kHz to about 700 kHz, from about 0.0001 kHz to about 600 kHz, from about 0.0001 kHz to about 500 kHz, from about 0.0001 kHz to about 400 kHz, from about 0.0001 kHz to about 300 kHz, from about 0.0001 kHz to about 200 kHz, from about 0.0001 kHz to about 100 kHz, from about 100 kHz to about 200 kHz, from about 200 kHz to about 300 kHz, from about 300 kHz to about 400 kHz, from about 400 kHz to about 500 kHz, from about 500 kHz to about 600 kHz, from about 600 kHz to about 700 kHz, from about 700 kHz to about 800 kHz, from about 800 kHz to about 900 kHz, from about 900 kHz to about 1000 kHz, from about 1 Hz to about 500 kHz, from about 1 kHz to about 500 kHz, from about 1 kHz to about 50 kHz, from about 1 Hz to about 50 kHz.

In one example of the disclosure, in a similar way to the activation signal used for electrical field stimulation, the activation signal used for magnetic fields can also be configured by a carrier signal (9) and a modulating signal (8). For example, the $f_{im}$, and the $f_{fm}$ are between 0.1 Hz and 500 kHz for both the carrier signal (9) and the modulating signal (8), with the carrier signal (9) optionally of an order of frequency greater than that of the modulating signal (8).

In an example of the method, in an example, in stage (d'), the NT can be between 5% and 60% and optionally between 25% and 50%. The applicable range values for NT for magnetic stimulation are the same used for NT in electromagnetic stimulation cited before in this document.

In another example of this method, in stage (e'), the range of frequencies between the lower tissue stimulation frequency ($f_{bx}$) and the upper tissue stimulation frequency ($f_{tx}$) correspond to the central tissue frequencies.

Additionally, the control unit can be programmed so that it chooses the initial stimulation frequency ($f_{im}$), the final tissue stimulation frequency ($f_{fm}$) and the frequency delta ($\Delta f_m$) and, optionally, these characteristics are set by a user and stored in a memory for application of the method.

A pulsing function may be used to activate the magnetic field, where the $f_{im}$, and the $f_{fm}$ are between 0.1 Hz and 1000 kHz, the $\Delta f_m$ has a range between 0.1 Hz and 1 kHz, the $\Delta t_m$ is between 1 second and 1 hour, and optionally between 1 minute and 1 hour.

In addition, it may be possible to use an activation signal for square wave shape frequency scan magnetic stimulation in a frequency from 1 Hz to 50 kHz. For frequencies from 1 Hz to 5 kHz, applying a variation of the duty cycle of between 0.4% and 5% for a maximum magnetic field intensity of 200 mT (milliteslas) equivalent to 2000 Gauss. Later, for frequencies from 5 kHz to 50 kHz, applying a variation of the duty cycle of between 5% and 25% for a maximum magnetic field intensity of 40 mT (milliteslas) equivalent to 400 Gauss. This frequency scan is applied for a $t_{max}$ of 1 hour and may be repeated each day, for 6 days.

Figure 16:
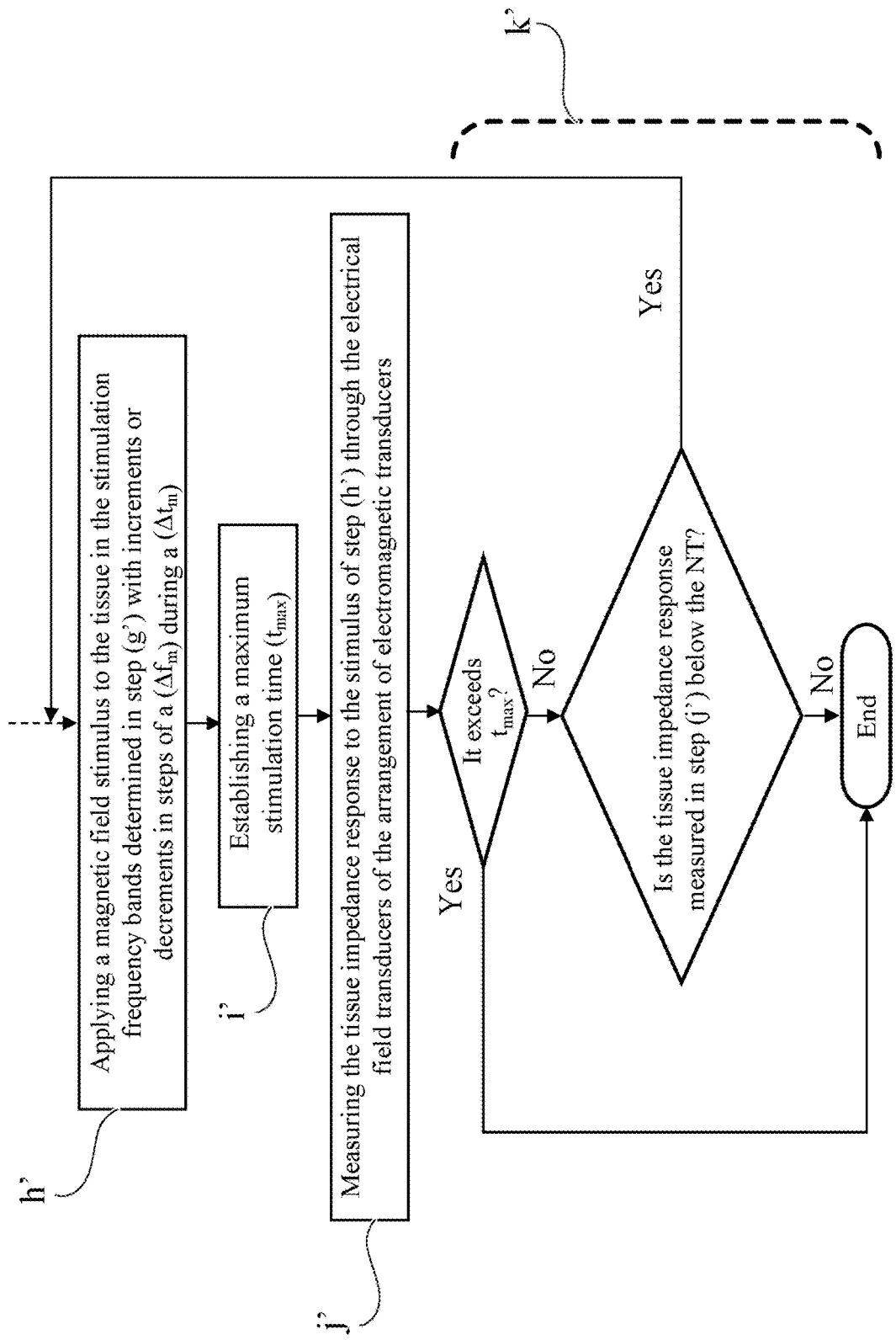
FIG. 16 shows a flow diagram of the method for tissue stimulation with frequency scan electric fields with additional stages in which stage k is disaggregated.

In addition to the above, and in reference to FIG. 15, in another example of the method, after stage (f'), the following stages are completed:

g') determining stimulation frequency bands based on the lower tissue stimulation frequencies ($f_{bx}$) determined in stage (e') along with the upper tissue stimulation frequencies ($f_{tx}$) determined in stage (f');

h') applying a magnetic field stimulus to a tissue through an arrangement of electromagnetic transducers that receive an activation signal, the frequency of which varies by the stimulation frequency bands determined in stage (g') with increments or decrements in steps of a frequency delta ($\Delta f_m$) during a time delta ($\Delta t_m$);

In another example of this method, and in reference to FIG. 16, after stage (h') of the method already described above, the following additional stages are followed:

i') establishing a maximum stimulation time ($t_{max}$), which makes it possible to protect the tissue from being overstimulated;

b') measuring the tissue impedance response to the stimulus of stage (h') via electrical field transducers of the arrangement of electromagnetic transducers.

k') verifying that the tissue impedance response measured in stage (j') in the stimulation frequency bands determined in stage (g') return to the tolerance (NT) established in stage (d') or exceed the maximum stimulation time ($t_{max}$).

In an example of an example of this method, $t_{max}$ in stage (i') can be between about 1 hour and about 18 hours. When referring to the $t_{max}$ "about" should be understood as a 5% variation of the maximum stimulation time.

In a specific example of this method, in stage (k'), the following verifications are performed:
- if the maximum stimulation time ($t_{max}$) is exceeded, then finalizing;
- if the maximum stimulation time ($t_{max}$) is not exceeded, and the tissue impedance response measured in stage (j') is below the tolerance (NT) established in stage (d'), repeating stage (h');
- if the tissue impedance response measured in stage (j') in the stimulation frequency bands determined in stage (g') exceed the tolerance (NT) established in stage (d'), then finalizing;

In addition to the above, tissue stimulation can also be applied by using spatial scanning, as described in the Colombian application NC2018/0001282 filed on 7 Feb. 2018.

In another example of the method, the activation signal obeys to a defined pattern, which follows the following steps:

A) defining an index for each magnetic field transducer in the arrangement of transducers;

B) selecting an index allocated to a transducer using the computing unit;

C) activating the magnetic field transducer that corresponds to the selected index, and stimulating the tissue using an initial tissue stimulation frequency ($f_i$) to a final tissue stimulation frequency ($f_{fm}$) in increments of a frequency delta ($\Delta f_m$) during a determined time delta ($\Delta t_m$);

D) increasing the value of the index and repeating step C) until all of the attributed indices have been used.

Alternatively, in a specific example of the method, in step D), the index value changes randomly and returns to step C).

Thus, the transducers can be activated randomly, and it is also possible to activate them in defined sequences, which will depend on the stimulation of the target tissue.

Optionally, in another example of the method for stimulating a tissue with magnetic fields, at stage (e'), the range of frequencies between the lower tissue stimulation frequency ($f_{bx}$) and the upper tissue stimulation frequency ($f_{tx}$) correspond to the central tissue frequencies.

Alternatively, in another example of the method for stimulating a tissue with magnetic fields, the activation signal for the electrical field transducers changes with tissue temperature feedback.

In another example of the method for stimulating a tissue with magnetic fields, the stimulated biological tissue is in an animal.

In another example of the method for stimulating a tissue with magnetic fields, the stimulated biological tissue is an animal.

Alternatively, another example of the method for stimulating a tissue with magnetic fields, the electromagnetic transducers are in contact with an external surface of the tissue.

In yet another example of the method for stimulating a tissue with magnetic fields the electromagnetic transducers are located a determined distance from an external surface of the biological tissue.

In a different example of the method for stimulating a tissue with magnetic fields, a first portion of the electromagnetic transducers are in contact with an external surface of the biological tissue and a second portion of the electromagnetic transducers are located a determined distance from the external surface of the biological tissue.

Optionally, in another example of the method for stimulating a tissue with magnetic fields, the electromagnetic transducers are activated according to a defined sequence.

Alternatively, in another example of the method for stimulating a tissue with electromagnetic fields, the electromagnetic transducers are activated randomly.

Optionally, in another example of the method for stimulating a tissue with magnetic fields, the activation signal is applied to each transducer at a determined time, sequentially, out of phase in relation to the other activation signal or to various stimulation signals, randomly or according to a program established for each one of the transducers.

In another example of this disclosure, it is possible to stimulate a tissue (3) with an arrangement of electromagnetic transducers (1) with electrical field transducers and magnetic field transducers applying a combination of electrical stimulation signals and magnetic stimulation signals that combine their characteristics on the basis of the feedback of magnetic field intensity applied to the tissue, the feedback of the tissue impedance or a combination of the two.

A third method for tissue stimulation is a method for stimulating a tissue with both electric fields and magnetic fields, the method comprising:

a*) applying an electric field and a magnetic field stimulus to a tissue through an arrangement of electromagnetic transducers that receive an activation signal, the parameters of which varies in time;

j') measuring the tissue impedance response to the stimulus of stage (h') via electrical field transducers of the arrangement of electromagnetic transducers.

c*) changing the parameters of the activation signal according to the tissue impedance response measured in stage (b*) though the computing unit and returning to stage (a*);

wherein the parameters of the activation signal are, modulation, phase, frequency, amplitude, duration, duty cycle and shape.

Additionally, it is possible to measure the temperature over the tissue in order to determine when the tissue being stimulated is affected and on the basis of a temperature level, the computing unit makes the decision to halt the stimulus to avoid tissue damage.

That is, it is possible that the activation signal of the magnetic transducers follow a pattern that changes with tissue temperature feedback, and this also applies to the activation signal of the electrical field transducers.

It can be possible to combine tissue stimulation with the frequency scan electrical fields method and the tissue stimulation with frequency scan magnetic fields method. In an example, the arrangement of electromagnetic transducers (1) comprises magnetic field transducers and electrical field transducers overlapped with each other, disposed orthogonally with each other, with their active faces in the direction of the tissue (3) in order to apply a combined stimulation by electrical and magnetic fields following an activation pattern.

Example of the Method of the Disclosure Applied in an Individual

Figure 11A:
FIG. 11A shows a photograph of an example of a type of malignant tissue on the neck of an individual before being stimulated with a frequency scan of electromagnetic fields.

In an example of this disclosure, tissue stimulation is performed in an individual with the following initial diagnosis of poorly differentiated malignant neoplasia shown in FIG. 11A. Immuno-histo-chemical markers present the following results:

Cytokeratin 5/6: positive in tumor cells;
P 63: positive in tumor cells;
High molecular weight cytokeratin: positive in tumor cells;
SOX10: negative in tumor cells; and,
Ber-EP4: negative in tumor cells.

The tissue was stimulated with a device for stimulating a tissue with electromagnetic fields which implements the method for stimulating a tissue of the present disclosure. The device used the following arrangement of electromagnetic transducers:

2 pairs of electrical field transducers disposed orthogonally (disposable 2×3.5 inch electrotherapy electrodes manufactured by Compass Health Brands Corp., for use as a disposable conductive adhesive interface between patient's skin and electrical stimulator), and
1 pair of magnetic field transducers disposed orthogonally to the two pairs of electrical field transducers.

According to described arrangement, a magnetic field stimulus and an electrical field stimulus are applied orthogonally to each other.

The computing unit of the device generates the activation signal according to a program established for each magnetic transducer. Specifically, the pair of magnetic field transducers was connected to a first and second channel of the device and received an activation signal having an amplitude of 72 Vpp (Peak-to-Peak Voltage) and applied in a frequency scan ranging from an initial tissue stimulation frequency $f_{im}$ equal to 1 Hz to a final tissue stimulation frequency $f_{fm}$ equal to 50 kHz. From said frequency scan two stimulation frequency bands were determined by the computing unit; the first stimulation frequency band corresponded to a frequency range from a first lower tissue stimulation frequency $f_{b1}$ equal to 1 Hz to a first upper tissue stimulation frequency $f_{t1}$ equal to 5 kHz, and the second stimulation frequency band corresponded to a frequency range from a second lower tissue stimulation frequency $f_{b2}$ equal to 5 kHz to a second upper tissue stimulation frequency $f_{t2}$ equal to 50 kHz.

The two pairs of electric field transducers were connected respectively to a third, fourth, fifth and sixth channel of the device. Each pair received an activation signal having an amplitude of 72 Vpp (Peak-to-Peak Voltage). The carrier signal was an alternating impulse train with a fixed frequency of 150 kHz modulated in PWM having a duty cycle of 15%; the modulating signal was a triangular waveform of varying frequency. This activation signal was applied in a frequency scan ranging from an initial tissue stimulation frequency $f_{ie}$ equal to 1 kHz to a final tissue stimulation frequency $f_{fe}$ equal to 500 kHz. From said frequency scan, three stimulation frequency bands were determined by the computing unit: the first stimulation frequency band corresponded to a frequency range from a first lower tissue stimulation frequency $f_{b1}$ equal to 1 kHz to a first upper tissue stimulation frequency $f_{t1}$ equal to 50 kHz; the second stimulation frequency band corresponded to a frequency range from a second lower tissue stimulation frequency $f_{b2}$ equal to 150 kHz to a second upper tissue stimulation frequency $f_{t2}$ equal to 250 kHz; and the third stimulation frequency band corresponded to a frequency range from a third lower tissue stimulation frequency $f_{b3}$ equal to 320 kHz to a third upper tissue stimulation frequency $f_{t3}$ equal to 420 kHz.

The measured average power delivered to the tissue of above example ranged between 0.2 W to 0.5 W. The electrode temperature never surpassed 40° C.

After determining the stimulation frequency bands, the device for stimulating a tissue with electromagnetic fields applied activation signals in each of these stimulation frequency bands for an hour each day for a total of 6 days. In all cases, the frequency delta (Δf) steps were 500 Hz, and the time delta (Δt) steps were 1 second.

Figure 11B:
FIG. 11B shows an example of a type of malignant tissue on the neck of the same individual of FIG. 11A, after being stimulated with a frequency scan of electromagnetic fields.

In reference to FIG. 11B, a photograph is shown of the same individual showing a marked reduction of the mass of the malignant tumor after the delivery schedule noted above. Additionally, the laboratory report after the stimulation was negative for metastasis.

Figure 11C:
FIG. 11C shows a tissue impedance signal which corresponds to the tissue impedance response over a single electrical field channel of the individual in an intermediate stage between FIG. 11A and FIG. 11B.

In reference to FIG. 11C, the graph shows a tissue impedance signal (34) which corresponds to the tissue impedance response across channels 5 and 6 to the third stimulation frequency band mentioned above (fb3=320 kHz; ft3=420 kHz), and correlates in time to an intermediate stage in the individual's response between FIG. 11A and FIG. 11B. As the graph shows, the tissue impedance signal (34) starts to show a drop-off at about 140 seconds, when the tissue stimulating frequency applied was about 320 kHz. This drop-off, or valley, lasted until about 340 seconds, when the tissue stimulating frequency applied reached about 420 kHz.

A trend was observed whereby the foregoing tissue impedance response valley was not bound to specific frequencies over the course of each application. Instead, slight frequency shifts of the tissue impedance response were observed, typically showing a +/−20% variation. Over the course of the 6 days of delivery, the tissue impedance valleys tended to disappear.

Figure 11D:
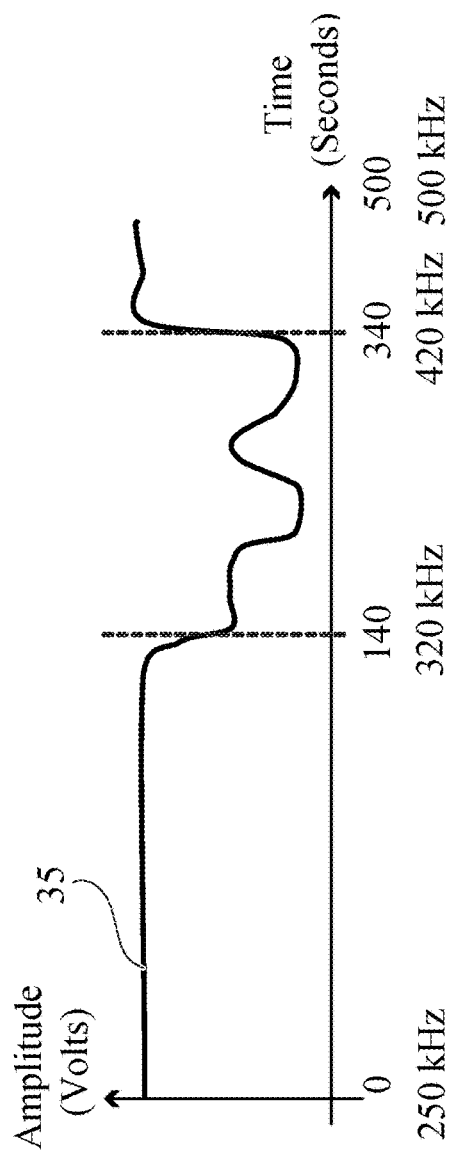
FIG. 11D shows a smoothed tissue impedance signal of tissue impedance signal shown in FIG. 11C.

FIG. 11D shows a smoothed tissue impedance response signal (35) and was achieved by averaging the tissue impedance response signal (34).

DEFINITIONS AND ACRONYMS

AM Amplitude Modulation
AMOLED Active Matrix Organic Light Emitting Diode
ASIC Application Specific Integrated Circuits
CPLD Complex Programmable Logic Devices
DSC Digital Signal Controllers
EEG Electroencephalogram.
EMF Electromagnetic Fields.
$f_{bx}$ Lower tissue stimulation frequencies: refers to the lowest frequency of a stimulation band the frequency scanning stimulation.
$f_{fe}$ Final tissue stimulation frequency: refers to the final frequency of the frequency scanning stimulation with electric fields.
$f_{fm}$ Final tissue stimulation frequency: refers to the final frequency of the frequency scanning stimulation with magnetic fields.
$f_{ie}$ Initial tissue stimulation frequency: refers to the starting frequency of the frequency scanning stimulation with electric fields.

$f_{im}$ Initial tissue stimulation frequency: refers to the starting frequency of the frequency scanning stimulation with magnetic fields.

FM Frequency Modulation

FPGA Field Programmable Gate Arrays $f_{tx}$ Upper tissue stimulation frequency: refers to the final frequency of the frequency scanning stimulation.

HID Human Interface Device

LCD Liquid Crystal Display

LED Light Emitting Diode

MFG Magnetic Field Generator.

NT Tolerance is a percentage value of the reference level value, which the method determines a $f_{bx}$ or $f_{tx}$ based on whether the tissue impedance response exceeds or not said percentage value.

OLED Organic Light Emitting Diode

PEMF Pulsed Electromagnetic Fields.

PM Phase Modulation

PPM Pulse Position Modulation

PSoC Programmable Systems on Chip

PWM Pulse Width Modulation

QD Quantum Display

SoC Systems on Chip

SPMF Programmed Magnetic Fields.

$\Delta f_e$ Frequency delta: refers to the increments or decrements in steps of the frequency of the frequency scanning stimulation with electric fields.

$\Delta f_m$ Frequency delta: refers to the increments or decrements in steps of the frequency of the frequency scanning stimulation with magnetic fields.

$\Delta t_e$ Time delta: refers to the duration or period of time of the frequency scanning stimulation with electric fields.

$\Delta t_m$ Time delta: refers to the duration or period of time of the frequency scanning stimulation with magnetic fields.

Reference level Refers to a value stablished by a user or computing unit for escalate or fitting or fixing the tissue impedance response in an amplitude range values to be presented or analyzed to a user.

Stimulation frequency bands Refers to a range of frequencies where the amplitude tissue impedance response falls below the tolerance.

This disclosure is not limited to the described the illustrated examples, since, as will be obvious to the person skilled in the art, there are possible variations and modifications that do not depart from the spirit of the disclosure, which is only defined by the following claims.

The invention claimed is:

1. A method for stimulating a tissue with electromagnetic fields, the method comprising:
   a) applying an electric field stimulus to a tissue through an arrangement of electromagnetic transducers that receives an activation signal, a frequency of which varies from an initial tissue stimulation frequency ($f_{ie}$) to a final tissue stimulation frequency ($f_{fe}$) with increments or decrements in steps of a frequency delta ($\Delta f_e$) during a time delta ($\Delta t_e$);
   b) measuring a tissue impedance response to the electric field stimulus of stage (a);
   c) establishing a reference level with the tissue impedance response measured in stage (b);
   d) establishing a tolerance (NT) to the reference level established in stage (c);
   e) determining lower tissue stimulation frequencies ($f_{bx}$) as a point where the tissue impedance response falls below the NT established in stage (d);
   f) determining upper tissue stimulation frequencies ($f_{tx}$) as a point where the tissue impedance response returns to the NT established in stage (d);
   g) determining stimulation frequency bands based on the $f_{bx}$ determined in stage (e) along with the $f_{tx}$ determined in stage (f)
   h) applying the electric field stimulus to the tissue through the arrangement of electromagnetic transducers that receive an activation signal, the frequency of which varies by the stimulation frequency bands determined in stage (g) with increments or decrements in steps of a $\Delta f_e$ during the $\Delta t_e$;
   i) establishing a maximum stimulation time ($t_{max}$);
   j) measuring the tissue impedance response to the electric field stimulus of stage (h), and
   k) verifying that the tissue impedance response measured in stage (j) in the stimulation frequency bands determined in stage (g) returns to the NT established in stage (d) or exceeds the $t_{max}$,
   wherein the $f_{tx}$ are greater than the $f_{bx}$ and "x" is a natural number greater than or equal to 1.

2. The method of claim 1, wherein the $f_{ie}$, the $f_{fe}$, the $\Delta f_e$, the $\Delta t_e$, the NT, the $f_{bx}$ and the $f_{tx}$ are established by a user in a processor, and stored in a memory connected to the processor.

3. The method of claim 1, wherein the NT is between about 25% and about 50%.

4. The method of claim 1, wherein at stage (a), the activation signal is selected from the group consisting of: a direct or alternating signal, a pulsed signal or non-alternating pulse trains, a squared wave signal with variation of a duty cycle, a triangular wave signal, a sawtooth wave signal, modulated by amplitude, modulated by frequency, modulated by phase, modulated by pulse positions, or combinations thereof.

5. The method of claim 1, wherein the $f_{ie}$ and $f_{fe}$ are between about 0.1 Hz and about 1000 kHz.

6. The method of claim 1, wherein the $\Delta f_e$ is a value between about 0.1 Hz and about 1 kHz.

7. The method of claim 1, wherein the $\Delta t_e$ is between about 1 second and about 1 hour.

8. The method of claim 1, wherein the $t_{max}$ is between about 1 hour and about 18 hours.

9. The method of claim 1, wherein stage (k) further comprises:
   if the $t_{max}$ is exceeded, then finalizing the application of the electric field stimulus to the tissue;
   if the $t_{max}$ is not exceeded, and the tissue impedance response measured in stage (j) is below the NT established in stage (d), repeating stage (h); and
   if the tissue impedance response measured in stage (j) in the stimulation frequency bands determined in stage (g) exceeds the NT established in stage (d), then finalizing the application of the electric field stimulus to the tissue.

10. The method of claim 1, wherein at stage (a), further comprises:
    applying a magnetic field stimulus to the tissue by means of an arrangement of electromagnetic transducers that receive an activation signal, the frequency of which varies from an initial tissue stimulating frequency ($f_{im}$) to a final tissue stimulation frequency ($f_{fm}$) with increments or decrements in steps of a frequency delta ($\Delta f_m$) during a time delta ($\Delta t_m$).

11. The method of claim 10, wherein the electromagnetic transducers comprise electrical field transducers and magnetic field transducers, wherein at stage (a), the magnetic field transducers are arranged such that they generate magnetic fields orthogonally to electrical fields generated by the electrical field transducers.

12. The method of claim 1, wherein at stage (e), a range of frequencies between the $f_{bx}$ and the $f_{tx}$ correspond to a plurality of central tissue frequencies.

13. The method of claim 1, wherein the activation signal for the electromagnetic transducers changes with tissue temperature feedback.

14. The method of claim 1, wherein the electromagnetic transducers are configured to be in contact with an external surface of the tissue.

15. The method of claim 1, wherein the electromagnetic transducers are configured to be located a determined distance from an external surface of the tissue.

16. The method of claim 1, wherein a first portion of the electromagnetic transducers are configured to be in contact with an external surface of the tissue and a second portion of the electromagnetic transducers are configured to be located a determined distance from the external surface of the tissue.

17. The method of claim 1, wherein the electromagnetic transducers are activated according to a defined sequence.

18. The method of claim 1, wherein the electromagnetic transducers are activated randomly.

19. The method of claim 1, wherein the activation signal is applied to each electromagnetic transducer at a determined time, sequentially, out of phase in relation to another activation signal or to various stimulation signals, randomly or according to a program established for each one of the electromagnetic transducers.

20. A method for stimulating a tissue with electromagnetic fields, the method comprising:
   a') applying a magnetic field stimulus to the tissue through an arrangement of electromagnetic transducers that receive an activation signal, a frequency of which varies from an initial tissue stimulation frequency ($f_{im}$) to a final tissue stimulation frequency ($f_{fm}$) with increments or decrements in steps of a frequency delta ($\Delta f_m$) during a time delta ($\Delta t_m$);
   b') measuring a tissue impedance response to the magnetic field stimulus through a plurality of electrical field transducers that are part of the arrangement of electromagnetic transducers;
   c') establishing a reference level with the tissue impedance response measured in stage (b');
   d') establishing a tolerance (NT) to the reference level established in stage (c');
   e') determining lower tissue stimulation frequencies ($f_{bx}$) as a point where the tissue impedance response falls below the NT established in stage (d');
   f) determining upper tissue stimulation frequencies ($f_{tx}$) as the point where the tissue impedance response returns to the NT established in stage (d');
   g') determining stimulation frequency bands based on the $f_{bx}$ determined in stage (e') along with the $f_{tx}$ determined in stage (f);
   h') applying the magnetic field stimulus to the tissue through the arrangement of electromagnetic transducers that receive an activation signal, the frequency of which varies by the stimulation frequency bands determined in stage (g') with increments or decrements in steps of the $\Delta f_m$ during the $\Delta t_m$;
   i') establishing a maximum stimulation time ($t_{max}$);
   j') measuring the tissue impedance response to the magnetic field stimulus of stage (h') by means of the plurality of electrical field transducers; and
   k') verifying that the tissue impedance response measured in stage (j') in the stimulation frequency bands determined in stage (g') returns to the NT established in stage (d') or exceeds the $t_{max}$,
   wherein the $f_{tx}$ are greater than the $f_{bx}$ and "x" is a natural number greater than or equal to 1.

21. The method of claim 20, wherein the $f_{im}$, the $f_{fm}$, the $\Delta f_m$, the $\Delta t_m$, the NT, the $f_{bx}$ and the $f_{tx}$ are established by a user in a processor, and stored in a memory connected to the processor.

22. The method of claim 20, wherein the NT is between about 25% and about 50%.

23. The method of claim 20, wherein, at stage (a') the activation signal is selected from the group consisting of: a direct or alternating signal, a pulsed signal or non-alternating pulse trains, a squared wave signal with variation of a duty cycle, a triangular wave signal, a sawtooth wave signal, modulated by amplitude, modulated by frequency, modulated by phase, modulated by pulse positions, or combinations thereof.

24. The method of claim 20, wherein the $f_{im}$, and the $f_{fm}$ are between about 0.1 Hz and about 1000 kHz.

25. The method of claim 20, wherein the $\Delta f_m$ is a value between about 0.1 Hz and about 1 kHz.

26. The method of claim 20, wherein the $\Delta t_m$ is between about 1 second and about 1 hour.

27. The method of claim 20, wherein the $t_{max}$ is between about 1 hour and about 18 hours.

28. The method of claim 20, wherein stage (k') comprises the following verifications:
   if the $t_{max}$ is exceeded, then finalizing the application of the magnetic field stimulus to the tissue;
   if the $t_{max}$ is not exceeded, and the tissue impedance response measured in stage (j') is below the NT established in stage (d'), repeating stage (h'); and
   if the tissue impedance response measured in stage (j') in the stimulation frequency bands determined in stage (g') exceed the NT established in stage (d'), then finalizing the application of the magnetic field stimulus to the tissue.

29. The method of claim 20, wherein at stage (g'), a range of frequencies between the $f_{bx}$ and the $f_{tx}$ correspond to central tissue frequencies.

30. The method of claim 20, wherein the activation signal for the electromagnetic transducers follows a pattern that changes with tissue temperature feedback.

31. The method of claim 20, wherein the activation signal obeys a defined pattern, which follows these steps:
   A) defining an index for each magnetic field transducer of the arrangement of electromagnetic transducers;
   B) selecting the index allocated to a particular magnetic field transducer using a processor;
   C) activating the magnetic field transducer that corresponds to the selected index, and stimulating the tissue using an $f_{im}$ to a $f_{fm}$ in increments of a $\Delta f_m$ during a fixed $\Delta t_m$; and
   D) increasing a value of the index and repeating step C) until all of the attributed indices have been used.

32. The method of claim 31, wherein at step D), the value of the index changes randomly and returns to step C).

33. The method of claim 20, wherein the electromagnetic transducers are configured to be in contact with an external surface of the tissue.

34. The method of claim 20, wherein the electromagnetic transducers are configured to be located a determined distance from an external surface of the tissue.

35. The method of claim 20, wherein a first portion of the electromagnetic transducers are configured to be in contact with an external surface of the tissue and a second portion of the electromagnetic transducers are configured to be located a determined distance from the external surface of the tissue.

36. The method of claim 20, wherein the electromagnetic transducers are activated according to a defined sequence.

37. The method of claim 20, wherein the electromagnetic transducers are activated randomly.

38. The method of claim 20, wherein the activation signal is applied to each electromagnetic transducer at a determined time, sequentially, out of phase in relation to another activation signal or to various stimulation signals, randomly or according to a program established for each one of the electromagnetic transducers.

39. A device for stimulating a tissue with electromagnetic fields, the device comprising:
   at least one processor;
   an external power source connected to the at least one processor;
   a decoupling circuit connected to the external power source and to the at least one processor;
   an arrangement of electromagnetic transducers connected to the at least one processor and to the decoupling circuit, the arrangement configured to be disposed over the tissue; and
   at least one non-transitory computer-readable media storing computer-executable instructions that, when executed by the at least one processor perform a method for stimulating the tissue with electromagnetic fields, the method comprising the stages of:
   a) applying an electric field stimulus to the tissue through the arrangement of electromagnetic transducers that receives an activation signal, a frequency of which varies from an initial tissue stimulation frequency ($f_{ie}$) to a final tissue stimulation frequency ($f_{fe}$) with increments or decrements in steps of a frequency delta ($\Delta f_e$) during a time delta ($\Delta t_e$);
   b) measuring a tissue impedance response to the electric field stimulus of stage (a);
   c) establishing a reference level with the tissue impedance response measured in stage (b);
   d) establishing a tolerance (NT) to the reference level established in stage (c);
   e) determining lower tissue stimulation frequencies ($f_{bx}$) as a point where the tissue impedance response falls below the NT established in stage (d);
   f) determining upper tissue stimulation frequencies ($f_{tx}$) as a point where the tissue impedance response returns to the NT established in stage (d); wherein the $f_{tx}$ are greater than the $f_{bx}$ and "x" is a natural number greater than or equal to 1;
   g) determining stimulation frequency bands based on the $f_{bx}$ determined in stage (e) along with the $f_{tx}$ determined in stage (f);
   h) applying the electric field stimulus to the tissue through the arrangement of electromagnetic transducers that receive an activation signal, the frequency of which varies by the stimulation frequency bands determined in stage (g) with increments or decrements in steps of a $\Delta f_e$ during the $\Delta t_e$;
   i) establishing a maximum stimulation time ($t_{max}$);
   j) measuring the tissue impedance response to the electric field stimulus of stage (h); and
   k) verifying that the tissue impedance response measured in stage (j) in the stimulation frequency bands determined in stage (g) returns to the NT established in stage (d) or exceeds the $t_{max}$.

40. The device of claim 39, wherein the NT is between about 25% and about 50%.

41. The device of claim 39, wherein the fie and the $\Delta f_e$ are between about 0.1 Hz and about 1000 kHz.

42. The device of claim 39, wherein the $\Delta f_e$ is a value between about 0.1 Hz and about 1 kHz.

43. The device of claim 39, wherein the $\Delta t_e$ is between about 1 second and about 1 hour.

44. The device of claim 39, wherein stage (k) comprises the following verifications:
   if the $t_{max}$ is exceeded, then finalizing the application of the electric field stimulus to the tissue;
   if the $t_{max}$ is not exceeded, and the tissue impedance response measured in stage (j) is below the NT established in stage (d), repeating stage (h); and
   if the tissue impedance response measured in stage (j) in the stimulation frequency bands determined in stage (g) exceed the NT established in stage (d), then finalizing the application of the electric field stimulus to the tissue.

45. The device of claim 39, further comprising a plurality of oscillators connected to the at least one processor, wherein each of the plurality of oscillators has an activation signal output.

46. The device of claim 39, wherein the at least one processor is connected to a peripheral device selected from the group consisting of: a memory unit, a database, a hard drive, a keyboard, a camera, a touchscreen display, a scanner, a display, and a printer.

47. The device of claim 39, wherein the arrangement of electromagnetic transducers comprises a plurality of electrical electric field transducers and a plurality of magnetic field transducers.

48. The device of claim 47, wherein the plurality of magnetic field transducers are arranged such that they generate magnetic fields orthogonally to electrical fields that are generated by the plurality of electrical field transducers.

49. The device of claim 39, wherein at stage (a), further comprising:
   applying a magnetic field stimulus to the tissue by means of an arrangement of electromagnetic transducers that receive an activation signal, the frequency of which varies from an initial tissue stimulating frequency ($f_{im}$) to a final tissue stimulation frequency ($f_{fm}$) with increments or decrements in steps of a frequency delta ($\Delta f_m$) during a time delta ($\Delta t_m$).

50. The device of claim 39, wherein a first portion of the electromagnetic transducers are configured to be in contact with an external surface of the tissue and a second portion of the electromagnetic transducers are configured to be located a determined distance from the external surface of the tissue.

51. A device for stimulating a tissue with electromagnetic fields, the device comprising:
   at least one processor;
   an external power source connected to the at least one processor;
   a decoupling circuit connected to the external power source and to the at least one processor; and
   an arrangement of electromagnetic transducers connected to the at least one processor and to the decoupling circuit, the arrangement is configured to be disposed over the tissue;

at least one non-transitory computer-readable media storing computer-executable instructions that, when executed by the at least one processor perform a method for stimulating the tissue with magnetic fields, the method comprising the stages of:

a') applying a magnetic field stimulus to the tissue through the arrangement of electromagnetic transducers that receive an activation signal, a frequency of which varies from an initial tissue stimulation frequency ($f_{im}$) to a final tissue stimulation frequency ($f_{fm}$) with increments or decrements in steps of a frequency delta ($\Delta f_m$) during a time delta ($\Delta t_m$);

b') measuring a tissue impedance response to the magnetic field stimulus through a plurality of electrical field transducers that are part of the arrangement of electromagnetic transducers;

c') establishing a reference level with the tissue impedance response measured in stage (b');

d') establishing a tolerance (NT) to the reference level established in stage (c');

e') determining lower tissue stimulation frequencies ($f_{bx}$) as a point where the tissue impedance response falls below the NT established in stage (d');

f) determining upper tissue stimulation frequencies ($f_{tx}$) as a point where the tissue impedance response returns to the NT established in stage (d');

g') determining stimulation frequency bands based on the $f_{bx}$ determined in stage (e') along with $f_{tx}$ determined in stage (f);

h') applying the magnetic field stimulus to a tissue through the arrangement of electromagnetic transducers that receive an activation signal, the frequency of which varies by the stimulation frequency bands determined in stage (g') with increments or decrements in steps of the $\Delta f_m$ during the $\Delta t_m$;

i') establishing a maximum stimulation time ($t_{max}$);

j') measuring the tissue impedance response to the magnetic field stimulus of stage (h') by means of the plurality of electrical field transducers; and k') verifying that the tissue impedance response measured in stage (j') in the stimulation frequency bands determined in stage (g') returns to the NT established in stage (d') or exceeds the $t_{max}$, wherein the $f_{tx}$ are greater than the $f_{bx}$ and "x" is a natural number greater than or equal to 1.

* * * * *